United States Patent
Gupta et al.

(10) Patent No.: US 6,855,269 B2
(45) Date of Patent: Feb. 15, 2005

(54) PHENYL ETHER-SUBSTITUTED HYDROXYPHENYL TRIAZINE ULTRAVIOLET LIGHT ABSORBERS

(75) Inventors: Ram Baboo Gupta, Stamford, CT (US); Hargurpreet Singh, Ansonia, CT (US); Russell C. Cappadona, Norwalk, CT (US)

(73) Assignee: Cytec Technology Corp., Wilmington, DE (US)

( * ) Notice: Subject to any disclaimer, the term of this patent is extended or adjusted under 35 U.S.C. 154(b) by 292 days.

(21) Appl. No.: 10/039,933

(22) Filed: Nov. 9, 2001

(65) Prior Publication Data

US 2003/0146412 A1 Aug. 7, 2003

(51) Int. Cl.$^7$ ................................................ C09K 3/00
(52) U.S. Cl. .................. 252/182.13; 252/380; 252/384; 544/180; 544/215; 544/216; 544/217; 544/218
(58) Field of Search ................................ 544/180, 215, 544/216, 217, 218; 252/182.13, 380, 384

(56) References Cited

U.S. PATENT DOCUMENTS

| | | | |
|---|---|---|---|
| 3,118,887 A | 1/1964 | Hardy et al. ................ 260/248 |
| 3,221,698 A | 12/1965 | Johns et al. .................... 260/47 |
| 3,244,708 A | 4/1966 | Duennenberger et al. ... 260/248 |
| 3,423,360 A | 1/1969 | Huber et al. ................... 260/47 |
| 3,843,371 A | 10/1974 | Piller et al. ................... 96/84 R |
| 3,896,125 A | 7/1975 | Helmo et al. ............. 260/249.5 |
| 4,161,592 A | 7/1979 | Evans et al. ................. 544/198 |
| 4,314,933 A | 2/1982 | Berner ................. 260/45.75 N |
| 4,344,876 A | 8/1982 | Berner ........................... 524/91 |
| 4,426,471 A | 1/1984 | Berner ........................... 524/91 |
| 4,426,472 A | 1/1984 | Berner ........................... 524/99 |
| 4,619,956 A | 10/1986 | Susi ............................... 524/87 |
| 4,740,542 A | 4/1988 | Susi ............................... 524/87 |
| 4,775,707 A | 10/1988 | Slongo et al. ................. 524/91 |
| 4,826,978 A | 5/1989 | Migdal et al. .............. 544/216 |
| 4,948,666 A | 8/1990 | Paul et al. ................... 428/334 |
| 4,962,142 A | 10/1990 | Migdal et al. .............. 524/100 |
| 5,004,770 A | 4/1991 | Cortolano et al. ............ 524/99 |
| 5,006,577 A | 4/1991 | Behrens et al. ............... 524/95 |
| 5,030,731 A | 7/1991 | Slongo et al. ............... 548/260 |
| 5,064,883 A | 11/1991 | Behrens et al. ............... 524/95 |
| 5,106,891 A | 4/1992 | Valet ............................. 524/91 |
| 5,106,972 A | 4/1992 | Burdeska et al. ........... 544/219 |
| 5,112,890 A | 5/1992 | Behrens et al. ............... 524/95 |
| 5,124,378 A | 6/1992 | Behrens et al. ............... 524/95 |
| 5,189,084 A | 2/1993 | Birbaum et al. ............ 524/100 |
| 5,198,498 A | 3/1993 | Valet et al. .................. 525/125 |
| 5,204,473 A | 4/1993 | Winter et al. ............... 546/188 |
| 5,288,868 A | 2/1994 | Reinehr et al. ............. 544/219 |
| 5,298,067 A | 3/1994 | Valet et al. .................. 106/506 |
| 5,322,868 A | 6/1994 | Valet et al. .................... 524/89 |
| 5,354,794 A | 10/1994 | Stevenson et al. .......... 524/100 |
| 5,356,995 A | 10/1994 | Valet et al. .................. 525/100 |
| 5,369,140 A | 11/1994 | Valet et al. .................... 522/75 |
| 5,376,710 A | 12/1994 | Slongo et al. ................. 524/87 |
| 5,420,204 A | 5/1995 | Valet et al. .................. 525/125 |
| 5,438,138 A | 8/1995 | Henneberger et al. ...... 544/217 |
| 5,461,151 A | 10/1995 | Waterman .................... 544/216 |
| 5,476,937 A | 12/1995 | Stevenson et al. .......... 544/216 |
| 5,478,935 A | 12/1995 | Reinehr et al. ............. 544/180 |
| 5,563,224 A | 10/1996 | Szita et al. .................. 525/480 |
| 5,585,422 A | 12/1996 | Falk et al. ................... 524/100 |
| 5,597,854 A | 1/1997 | Birbaum et al. ............ 524/100 |
| 5,637,706 A | 6/1997 | Stevenson et al. .......... 544/216 |
| 5,686,233 A | * 11/1997 | Valet et al. .................. 430/512 |
| 5,726,309 A | 3/1998 | Stevenson et al. .......... 544/216 |
| 5,959,008 A | * 9/1999 | Birbaum et al. ............ 524/100 |
| 6,096,886 A | 8/2000 | Cohen ........................ 544/112 |
| 6,117,997 A | * 9/2000 | Bulliard et al. ............. 544/216 |
| 6,184,375 B1 | * 2/2001 | Huglin et al. ............... 544/116 |
| 6,225,468 B1 | 5/2001 | Gupta et al. ................ 544/216 |
| 6,284,821 B1 | * 9/2001 | Huglin et al. ............... 524/100 |

FOREIGN PATENT DOCUMENTS

| | | |
|---|---|---|
| EP | 0577559 A2 | 6/1993 |
| EP | 0395938 B1 | 1/1996 |
| EP | 0704437 A2 | 4/1996 |
| EP | 0704437 A3 | 10/1996 |
| EP | 0444323 B1 | 3/1997 |
| EP | 0 434608 B1 | 4/1997 |
| EP | 0779280 A1 | 6/1997 |
| EP | 0649841 B1 | 5/2001 |
| GB | 884802 | 12/1961 |
| GB | 1028923 | 3/1963 |
| GB | 2293823 A | 4/1996 |
| JP | 09059263 A | 3/1997 |
| JP | 160452 A | 11/2000 |
| WO | WO 96/28431 | 9/1996 |
| WO | WO 99/67227 | 6/1999 |
| WO | WO 00/14074 | 9/1999 |
| WO | WO 99/67226 | 12/1999 |
| WO | WO 00/29392 | 5/2000 |

OTHER PUBLICATIONS

Y. Chang et al., "Hyperbranched Poly(ether sulfone) with 1,3,5–s–Triazine Moiety," Korea Polymer Journal, vol. 8, No. 3, pp 142–146 (2000).

H. Brunetti and C. E. Lüthi, "Die Synthese von asymmetrisch substituierten o–Hydroxyphenyl–s–triazinen," Helvetica Chimica Acta—vol. 55 (1972), pp. 1566–1595.

Shigeo Tanimoto and Masato Yamagata, "Synthesis of Ultraviolet Absorber Having 2–(2–Hydroxyphenyl)–1,3, 5–Triazine Structure as a Functional Moiety," vol. 40, No. 12, (1995), pp. 339ff.

* cited by examiner

*Primary Examiner*—Cephia D. Toomer
(74) *Attorney, Agent, or Firm*—James A. Jubinsky; Fran Wasserman; Claire M. Schultz

(57) ABSTRACT

This invention relates generally to phenyl ether substituted triazines compounds and compositions containing same and their use to protect against degradation by environmental forces. A method for stabilizing a material by incorporating such triazines is also disclosed.

30 Claims, No Drawings

PHENYL ETHER-SUBSTITUTED HYDROXYPHENYL TRIAZINE ULTRAVIOLET LIGHT ABSORBERS

FIELD OF THE INVENTION

This invention relates generally to novel triazine ultraviolet (UV) light absorbers. More particularly, this invention relates to a 1,3,5-hydroxyphenyl triazine UV light absorbers substituted with phenyl ether and their use to protect against degradation by environmental forces, including ultraviolet light, actinic radiation, oxygen, moisture, atmospheric pollutants and combinations thereof.

BACKGROUND OF THE INVENTION

Description of Related Art

Exposure to sunlight and other sources of ultraviolet radiation is known to cause degradation of a variety of materials, especially polymeric materials. For example, polymeric materials such as plastics often discolor and may become brittle as a result of exposure to ultraviolet light. Accordingly, a large body of art has been developed directed towards materials such as ultraviolet light absorbers and stabilizers that are capable of inhibiting such degradation.

A class of materials known to be ultraviolet light absorbers are o-hydroxyphenyltriazines, in which at least one substituent on the 1, 3 or 5 carbon on the triazine ring is a phenyl group with a hydroxyl group ortho to the point of attachment to the triazine ring. In general this class of materials is well known in the art. Disclosures of a number of such trisaryl-1,3,5-triazines can be found in the patent literature such as disclosed in U.S. Pat. Nos. 3,843,371 and 3,896,125.

Typically, the aforementioned aryl ring with the hydroxyl group ortho to the point of attachment to the triazine ring is based on resorcinol and, consequently, this aryl ring also contains a second substituent (either a hydroxyl group or a derivative thereof) para to the point of attachment to the triazine ring. For example, U.S. Pat. Nos. 3,118,837 and 3,244,708 disclose p-alkoxy-o-hydroxyphenyl triazines with improved UV protection, but many embodiments of such triazines exhibit poor compatibility and solubility, and poor yellowing performance.

This para-substituent can be "non-reactive," as in the case of an alkyloxy group, or "reactive" as in the case of a hydroxyalkyloxy (active hydrogen reactive site) or (meth) acryloyl (ethylenic unsaturation reactive site) group. For the purposes of the present invention, the former are referred to as "non-bondable" substituted triazines and the latter are referred to as "bondable" substituted triazines.

Low volatility is an important characteristic of stabilizers used in any applications where high temperatures are encountered. High temperatures are used in the processing of thermoplastics and in the curing of thermoset resins and coatings. High temperatures are also often present in the end-use applications for the stabilized material. Low volatility will prevent loss of the stabilizer during processing, curing, and high temperature end-uses. Besides reducing losses of stabilizer during processing or curing, low volatility will minimize processing problems such as die lip build-up and plate-out.

Many polymer additives (such as ultraviolet light stabilizers) migrate out of the polymer substrate to be protected, or are adsorbed (chemically or physically) by one or more systems components (such as pigments), thereby diminishing their effectiveness. Such migration and adsorption problems are examples of the general problems of lack of solubility and compatibility found for many commercial polymer additives.

Bondable triazines are well known in the art. For example, U.S. Pat. Nos. 3,423,360; 4,962,142 and 5,189,084 disclose various bondable and the incorporation of these compounds into polymers by chemical bonding. Bondable stabilizers have a potential advantage in this respect in that, depending on the bondable functionality and the particular polymer system to be stabilized, they can be chemically incorporated into a polymer structure via reaction of the bondable functionality either during polymer formation (such as in the case of polymerizing monomers or a crosslinking polymer system) or subsequently with a preformed polymer having appropriate reactive functionality. Accordingly, due to such bonding, migration of these UV absorbers between layers of multi-layer coatings and into polymer substrates is greatly reduced.

This invention discloses a novel class of triazine UV absorbers containing at least one substituent on the triazine derived from phenyl ether or substituted phenyl ether, which have been found to have better performance than some of the similar commercial triazine UV absorbers.

SUMMARY OF THE INVENTION

The present invention provides a new class of hydroxyphenyl substituted triazines depicted below, in which a substituent attached to the hydroxyphenyl triazine ring is based on phenyl ether:

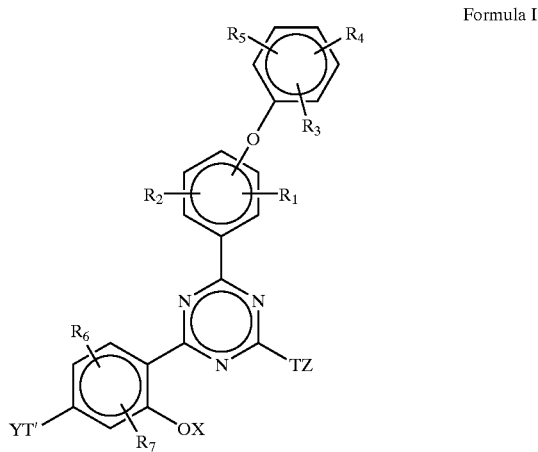

Formula I where $R_1$, $R_2$, $R_3$, $R_4$, $R_5$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_1$ and $R_2$, $R_3$ and $R_4$, or $R_4$ and $R_5$, taken together being a part of a saturated or unsaturated fused carbocyclic ring optionally containing O, N, or S atoms in the ring;

each of T and T' is independently a direct bond, oxygen, NR, sulfur or a functional group containing these elements;

X is independently selected from hydrogen and a blocking group;

each of Y, $R_6$ and $R_7$ are independently a hydrogen, hydrocarbyl group, a functional hydrocarbyl group, halogen, hydroxyl, cyano, —O(hydrocarbyl), —O(functional hydrocarbyl), —N(hydrocarbyl)$_2$, —N(functional hydrocarbyl)$_2$, —N(hydrocarbyl) (functional hydrocarbyl), —S(hydrocarbyl), —S(functional hydrocarbyl), —SO$_2$(hydrocarbyl), —SO$_2$(hydrocarbyl), —SO$_3$(hydrocarbyl), —SO$_3$ (functional hydrocarbyl), —CO$_2$(hydrocarbyl), —CO$_2$ (functional hydrocarbyl), —CO(hydrocarbyl), —CO (functional hydrocarbyl, —OCO(hydrocarbyl), —OCO(functional hydrocarbyl), —CONH$_2$, —CONH (hydrocarbyl), —CONH(functional hydrocarbyl), —CON(hydrocarbyl)$_2$, —CON(hydrocarbyl) (functional hydrocarbyl), —CON(functional hydrocarbyl)$_2$, —S(functional hydrocarbyl), —SO$_2$ (functional hydrocarbyl), —SO$_3$(functional hydrocarbyl), or a hydrocarbyl group substituted by any of the above groups;

Z is Y,

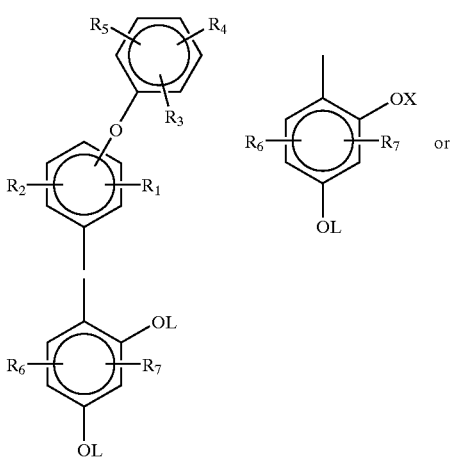

and where L is hydrogen, a hydrocarbyl of 1 to 24 carbon atoms, or a functional hydrocarbyl of 1 to 24 atoms.

DETAILED DESCRIPTION OF THE INVENTION

The present invention provides a new class of hydroxyphenyl substituted triazines depicted below, which are suitable to be used as UV light stabilizers, in which a substituent attached to the hydroxyphenyl triazine ring is based on phenyl ether:

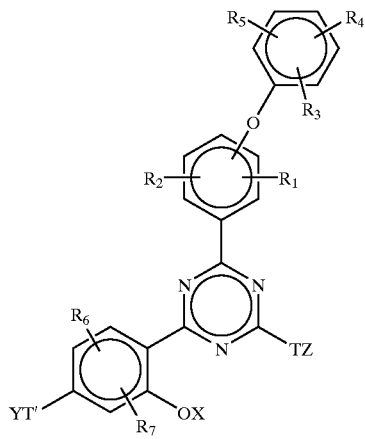

Formula I where $R_1$, $R_2$, $R_3$, $R_4$, $R_5$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, SO$_2$R, SO$_3$H, SO$_3$M, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_1$ and $R_2$, $R_3$ and $R_4$, or $R_4$ and $R_5$, taken together being a part of a saturated or unsaturated fused carbocyclic ring optionally containing O, N, or S atoms in the ring;

each of T and T' is independently a direct bond, oxygen, NR, sulfur or a functional group containing these elements;

X is independently selected from hydrogen and a blocking group;

each of Y, $R_6$ and $R_7$ are independently a hydrogen, hydrocarbyl group, a functional hydrocarbyl group, halogen, hydroxyl, cyano, —O(hydrocarbyl), —O(functional hydrocarbyl), —N(hydrocarbyl)$_2$, —N(functional hydrocarbyl)$_2$, —N(hydrocarbyl) (functional hydrocarbyl), —S(hydrocarbyl), —S(functional hydrocarbyl), —SO$_2$(hydrocarbyl), —SO$_2$(hydrocarbyl), —SO$_3$(hydrocarbyl), —SO$_3$ (functional hydrocarbyl), —CO$_2$ (hydrocarbyl), —CO$_2$ (functional hydrocarbyl), —CO(hydrocarbyl), —CO (functional hydrocarbyl, —OCO(hydrocarbyl), —OCO(functional hydrocarbyl), —CONH$_2$, —CONH (hydrocarbyl), —CONH(functional hydrocarbyl), —CON(hydrocarbyl)$_2$, —CON(hydrocarbyl) (functional hydrocarbyl), —CON(functional hydrocarbyl)$_2$, —S(functional hydrocarbyl), —SO$_2$ (functional hydrocarbyl), —SO$_3$(functional hydrocarbyl), or a hydrocarbyl group substituted by any of the above groups.

Preferably, T' is an oxygen atom and Y is a group L where L is defined below.

Also preferably, T is a direct bond and Z is Y, or TZ has the Formulas IIa, IIb and IIc:

Formula IIa

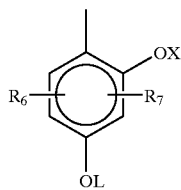

Formula IIb

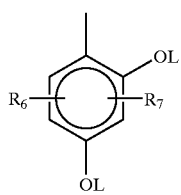

Formula IIc

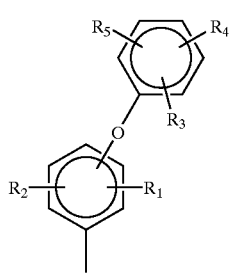

L is selected from the group consisting of: hydrogen; an alkyl of 1 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an alkenyl of 2 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain;

an aralkyl of 7 to 24 carbon atoms optionally substituted by one or more hydroxy, alkoxy, chloro, cyano, carboxy, carboalkoxy, amino, amido, carbamato, or epoxy groups, and which may contain one or more carbonyl groups, oxygen atoms or nitrogen atoms in the chain;

a polyoxyalkylene radical of the Formula XII $$-CH_2-CH(OH)-CH_2-O-(CH_2-(CH_2)_u-O-)_{mm}-D_1 \quad (XII)$$

wherein $D_1$ is hydrogen,

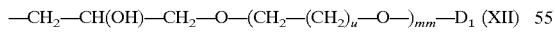

a polyoxyalkylene radical of the Formula XIII $$-CO-(CH_2)_u-O-(CH_2-(CH_2)_u-O-)_{mm}-D_2 \quad (XIII)$$

wherein $D_2$ is $-(CH_2)_u-CO-R^{22}$ or $R^{25}$;

a polyoxyalkylene radical of the Formula VIII $$-YY-O-CO-(CH_2)_u-O-(CH_2-(CH_2)_u-O-)_{mm}-D_3 \quad (XIV)$$

wherein $D_3$ is $-(CH_2)_u-CO-R^{22}$ or $R^{25}$;

a polyoxyalkylene radical of the Formula XV $$-(CH_2)_{kk}-CH(R^{21})-CO-B_1-(C_{nn}H_{2nn}-O-)_{mm}-C_{nn}H_{2nn}-B_1-D_4 \quad (XV)$$

wherein $D_4$ is hydrogen or $R^{25}$;

a polyoxyalkylene radical of the Formula XVI $$-CO-CH_2-CH_2-NH-(C_{nn}H_{2nn}-O-)_{mm}-C_{nn}H_{2nn}-D_5 \quad (XVI)$$

wherein $D_5$ is $-NH_2$, $-NH-(CH_2)_2-COO-R^{23}$ or $-O-R^{25}$;

a polyoxyalkylene radical of the Formula XVII $$-YY-O-CO-CH_2-CH_2-NH-(C_{nn}H_{2nn}-O-)_{mm}-C_{nn}H_{2nn}-D_5 \quad (XVII)$$

wherein $D_5$ is as defined under Formula XVI;

a polyoxyalkylene radical of the Formula XVIII $$-(C_{nn}H_{2nn}-O-)_{mm}-C_{nn}H_{2nn}-D_6 \quad (XVIII)$$

wherein $D_6$ is $-NH-CO-R^{24}$, $-OR^{25}$, OH or H;

a polyoxyalkylene radical of the Formula XIX $$-CH(R_{17})-CH_2-(OCH(R_{17})-CH_2)_m-D_7 \quad (XIX)$$

wherein $D_7$ is $-OR^{25}$, $-NHCOR^{24}$ or $-OCH_2CH_2OR^{25}$;

$R^{21}$ is hydrogen or $C_1-C_{16}$ alkyl;

$R^{22}$ is halogen or $-O-R^{23}$;

$R^{23}$ is hydrogen, $C_1-C_6$ alkyl, $C_3-C_6$ alkenyl, aryl, or aryl-$C_1-C_4$-alkyl;

$R^{24}$ is hydrogen, $C_1-C_{12}$ alkyl or aryl;

$R^{25}$ is $C_1-C_{16}$ alkyl, $C_5-C_{12}$ cycloalkyl, $C_3-C_6$ alkenyl, $C_1-C_{12}$ alkylaryl or aryl-$C_1-C_4$ alkyl;

$R^{26}$ is hydrogen or $C_1-C_4$ alkyl;

$R^{27}$ is hydrogen, $C_1-C_{18}$ alkyl, $C_3-C_6$ alkenyl, $C_1-C_{18}$ alkoxy, halogen or aryl-$C_1-C_4$-alkyl;

$R^{28}$ and $R^{29}$ independently of one another are hydrogen, $C_1-C_{18}$ alkyl, $C_3-C_6$ alkenyl, $C_1-C_{18}$ alkoxy, or halogen;

$R^{30}$ is hydrogen, $C_1-C_4$ alkyl or CN;

YY is unsubstituted or substituted $C_2-C_{20}$ alkyl;

kk is zero or an integer from 1–16;

$B_1$ is O or NH;

mm is an integer from 2 to 60;

nn is an integer from 2 to 6;

u is an integer from 1 to 4.

A preferred embodiment of the present invention is Formula IV below where the substituents are defined above:

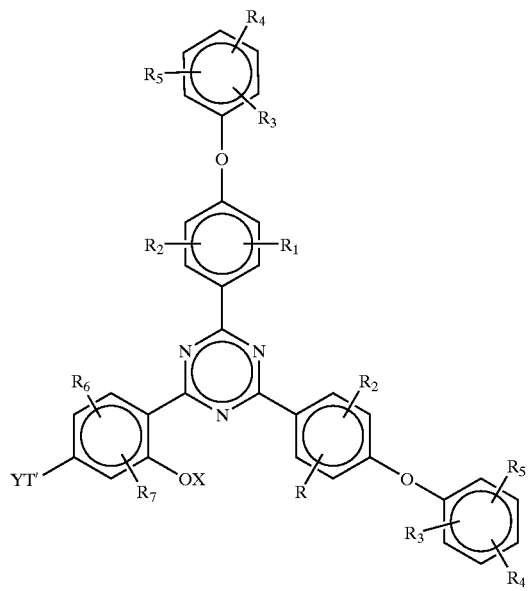

Formula IV

Another preferred embodiment of the present invention is Formula V below where the substituents are defined above:

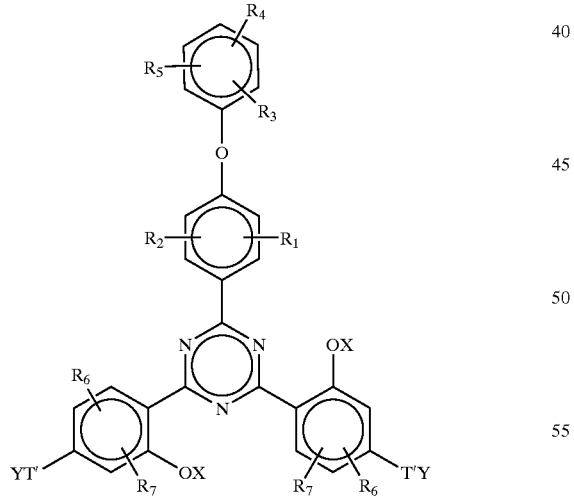

Formula V

More preferred Formulas IV and V are when $R_1$ to $R_7$ and X are hydrogen, T is oxygen and Y is L. More preferably L is a $C_1$ to $C_{12}$ alkyl or hydroxyalkyl.

The phenyl ether-substituted triazines of the present invention further comprise oligomeric species of Formulas (VI) and (VII):

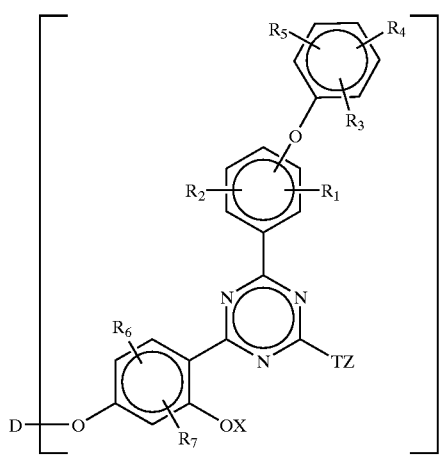

(Formula VI)

where $R_1$ to $R_7$, T, Z, X are defined above and where r is an integer between 2 and 4;

when r is 2, D is selected from the group consisting of $C_2$–$C_{16}$ alkyl, $C_4$–$C_{12}$ alkenyl, xylylene, $C_3$–$C_{20}$ alkyl which is interrupted by one or more oxygen atoms, hydroxy-substituted $C_3$–$C_{20}$ alkyl which is interrupted by one or more oxygen atoms, —CH$_2$CH(OH)CH$_2$O—R$^{15}$—OCH$_2$CH(OH)CH$_2$, —CO—R$^{16}$—CO—, —CO—NH—R$^{17}$—NH—CO—, —(CH$_2$)$_s$—COO—R$^{18}$—OCO—(CH$_2$)$_s$— a polyoxyalkylene bridge member of the Formula XX

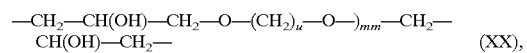

a polyoxyalkylene bridge member of the Formula XXI

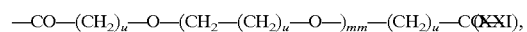

a polyoxyalkylene bridge member of the Formula XXII

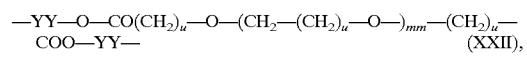

a polyoxyalkylene bridge member of the Formula XXIII

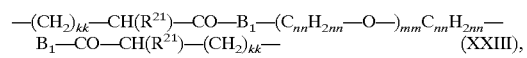

a polyoxyalkylene bridge member of the Formula XXIV

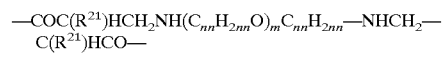

a polyoxyalkylene bridge member of the Formula XXV

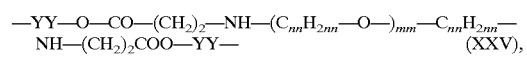

a polyoxyalkylene bridge member of the Formula XXVI

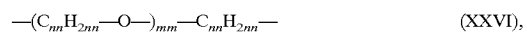

and a polyoxyalkylene bridge member of the Formula XXVII

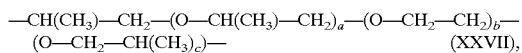

wherein a+c=2.5 and b=8.5 to 40.5 or a+c=2 to 33 and b=0, $R^{21}$ is hydrogen or $C_1$–$C_{16}$ alkyl, $R^{22}$ is halogen or —O—$R^{23}$, $R^{23}$ is hydrogen, $C_1$–$C_6$ alkyl, $C_3$–$C_6$ alkenyl, aryl, or aryl-$C_1$–$C_4$-alkyl, $R^{24}$ is hydrogen, $C_1$–$C_{12}$ alkyl or aryl, $R^{25}$ is $C_1$–$C_{16}$ alkyl, $C_5$–$C_{12}$ cycloalkyl, $C_3$–$C_6$ alkenyl, $C_1$–$C_{12}$ alkylaryl or aryl-$C_1$–$C_4$ alkyl, $R^{26}$ is hydrogen or $C_1$–$C_4$ alkyl, $R^{27}$ is hydrogen, $C_1$–$C_{18}$ alkyl, $C_3$–$C_6$ alkenyl, $C_1$–$C_{18}$ alkoxy, halogen or aryl-$C_1$–$C_4$ alkyl, $R^{28}$ and $R^{29}$ independently of one another are hydrogen, $C_1$–$C_{18}$ alkyl, $C_3$–$C_6$ alkenyl, or $C_1$–$C_{18}$ alkoxy, or halogen;

$R^{30}$ is hydrogen, $C_1$–$C_4$ alkyl or CN,

YY is unsubstituted or substituted $C_2$–$C_{20}$ alkyl, kk is zero or an integer from 1–16, $B_1$ is O or NH, mm is an integer from 2 to 60, nn is an integer from 2 to 6, u is an integer from 1 to 4;

when r is 3, D is —[—$(CH_2)_s$—COO—$]_3$—$R^{19}$ and when r is 4, D is —[—$(CH_2)_s$—COO—$]_4$—$R^{20}$ wherein $R^{19}$ is $C_3$–$C_{10}$ alkanetriyl and $R^{20}$ is $C_4$–$C_{10}$alkanetetryl; and s is 1–6;

$R^{15}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl, or phenylene-XX-phenylene wherein XX is —O—, —S—, —$SO_2$—, —$CH_2$—, or —$C(CH_3)_2$—;

$R^{16}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl provided that when r is 3 the alkenyl has at least 3 carbons;

$R^{17}$ is $C_2$–$C_{10}$ alkyl, phenyl, naphthyl, diphenyl, or $C_2$–$C_6$ alkenyl, methylenediphenylene, or $C_4$–$C_{15}$ alkylphenyl; and $R^{17}$ is $C_2$–$C_{10}$ alkyl, or $C_4$–$C_{20}$ alkyl interrupted by one or more oxygen atoms.

Formula VII

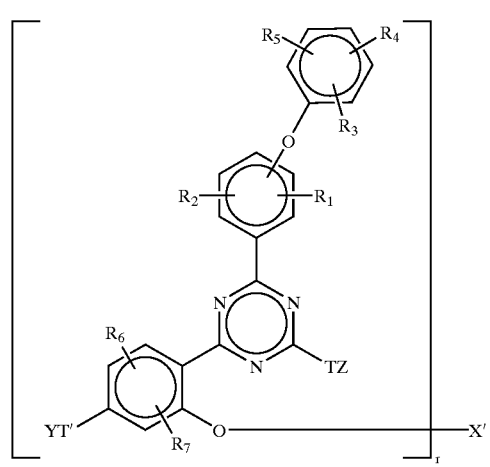

wherein T, T', Y, Z, $R_1$–$R_7$, are as defined above; r is 2 or 3; when r is 2, X' is —CO—$R^{16}$—CO—, —$CO_2$—$R^{16}$—$CO_2$—, —$SO_2$—$R^{16}$—$SO_2$—, —CO—NH—$R^{17}$—NH—CO—, a polyoxyalkylene bridge member of Formula —CO—$(CH_2)_u$—O—$(CH_2$—$(CH_2)_u$—O—$)_{mm}$—$(CH_2)_u$—CO—, or

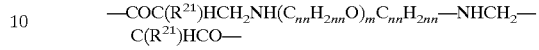

when r=3, X' is:

wherein $R^{16}$, $R^{17}$, $R^{18}$, and $R^{19}$ are as defined above.

The triazines of the present invention also comprise oligomeric species of the Formulas (VIII) and (IX):

Formula VIII

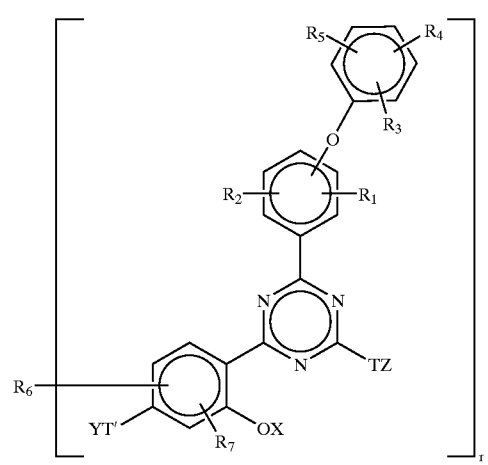

wherein T, T', Y, Z, $R_1$ to $R_7$, and X, are as defined above;

$R_6$ is selected from the group consisting of straight chain alkyl of 1 to 12 carbon atoms, branched chain alkyl of 1 to 12 carbon atoms, cycloalkyl of 5 to 12 carbon atoms, alkyl substituted by cyclohexyl, alkyl interrupted by cyclohexyl, alkyl substituted by phenylene, alkyl interrupted by phenylene, benzylidene, —S—, —S—S—, —S—E—S—, —SO—, —$SO_2$—, —SO—E—SO—, —$SO_2$—E—$SO_2$—, —$CH_2$—NH—E—NH—$CH_2$, and

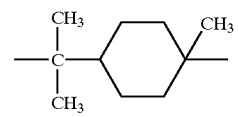

wherein E is selected from the group consisting of alkyl of 2 to 12 carbon atoms, cycloalkyl of 5 to 12 carbon atoms, alkyl interrupted by cyclohexyl of 8 to 12 carbon atoms, alkyl terminated by cyclohexyl of 8 to 12 carbon atoms; and r is an integer between 2 and 4.

Formula IX

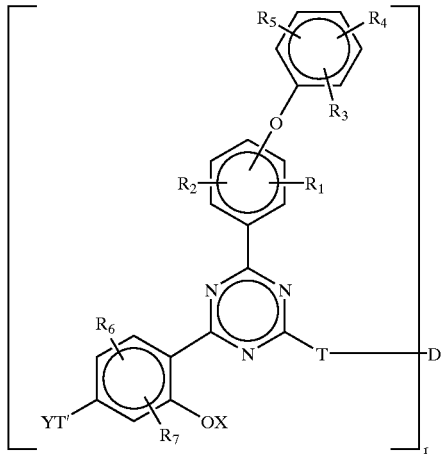

wherein Y, X, and $R_1$ to $R_7$ are defined above;

each of T and T' is independently a direct bond, oxygen, NR, sulfur or a functional group containing these elements;

r is an integer between 2 and 4;

when r is 2, D is selected from the group consisting of $C_2$–$C_{16}$alkylene, $C_4$–$C_{12}$alkenylene, xylylene, $C_3$–$C_{20}$alkylene which is interrupted by one or more oxygen atoms, hydroxy-substituted $C_3$–$C_{20}$alkylene which is interrupted by one or more oxygen atoms, —$CH_2CH(OH)CH_2O$—$R^{15}$—$OCH_2CH(OH)CH_2$—, —CO—$R^{16}$—CO—, —CO—NH—$R^{17}$—NH—CO—, and —$(CH_2)_s$—COO—$R^{18}$—OCO—$(CH_2)_s$—; and when r is 3, D is —[—$(CH_2)_s$—COO—]$_3$—$R^{19}$ and when r is 4, D is —[—$(CH_2)_s$—COO—]$_4$—$R^{20}$ wherein $R^{19}$ is $C_3$–$C_{10}$alkanetriyl and $R^{20}$ is $C_4$–$C_{10}$alkanetetryl;

s is 1–6;

$R^{15}$ is $C_2$–$C_{10}$ alkylene phenylene or a phenylene-x-phenylene- group, wherein X is —O—, —S—, —$SO_2$—, —$CH_2$—, or —$C(CH_3)_2$—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene or $C_2$–$C_6$ alkenylene;

$R^{17}$ is $C_2$–$C_{10}$ alkylene, phenylene, naphthylene, methylenediphenylene or $C_7$–$C_{15}$ alkylphenylene, and $R^{18}$ is $C_2$–$C_{10}$ alkylene or $C_4$–$C_{20}$ alkylene which is interrupted by one or more oxygen atoms.

The triazines of the present invention may optionally have the added benefit of being capable of being chemically bonded to appropriate polymer systems via functionality attached to the triazine groups (e.g., by a hydroxyl, ethylenic unsaturated and/or activated unsaturated group in one or more of Y or Z).

The triazines of the present invention may in general be prepared via a number of procedures well known in the art, for example, those described in Brunetti, H; Luethi, C.; *Helv. Chemica Acta*, 55 (1972) pp. 1566–1595; Tanimoto, S.; Yamagata, M. Senryo to Yakahin, 40 (1995) pp 339ff; U.S. Pat. Nos. 5,106,972; 5,288,868; 5,438,138 and 5,478,935; EP 395,938; EP 577,559; EP 649,841; EP 779,280; WO 9,628,431; GB 884,802; WO 00/29392 and Japanese Patent Kokai Tokkyo Koho 9,059,263 all of which are incorporated herein by reference for all purposes as if fully set forth. The preferred method is the procedure in WO/29392.

The novel triazines of the present invention are particularly useful as ultraviolet light absorber agents for stabilizing a wide variety of materials including, for example, organic compounds, oils, fats, waxes, cosmetics, dyes and biocides, and particularly various organic polymers (both cross-linked and non-cross-linked) used in applications such as photographic materials, plastics, fibers or dyed fibers, rubbers, paints and other coatings, and adhesives. The present invention, consequently, also relates to (1) a method of stabilizing a material which is subject to degradation by actinic radiation (e.g., an organic material such as an organic polymer in the form of a film, fiber, shaped article or coating) by incorporating into said material an amount of an actinic radiation stabilizer composition effective to stabilize the material against the effects of actinic radiation, wherein the actinic radiation stabilizer composition comprises the inventive triazines; and (2) the material so stabilized.

The novel triazines of the present invention are also effective as ultraviolet light screening agents in applications such as sunscreens and other cosmetic preparations, capstock layers for extruded polymers, dyed fibers and laminated UV-screening window films, among others. The present invention, consequently, also relates (1) to a method of protecting a substrate against degradation by actinic radiation by applying to the substrate an actinic radiation screening layer (e.g., a coating film or capstock layer) containing an actinic radiation screening composition in an amount effective to reduce the amount of actinic radiation impinging on the substrate, wherein the actinic radiation screening composition comprises the inventive triazines; and (2) the substrate so protected.

The novel triazines of the present invention may also be employed to form light stabilizing compositions. Such light stabilizing compositions may include a variety of other components known in the art including other ultraviolet light absorbers of the triazine class, other ultraviolet light absorbers of different classes (e.g. benzotriazoles, benzophenones), hindered amine light stabilizers, radical scavengers, antioxidants and the like.

The term "hydrocarbyl" in the context of the present invention, and in the above formulas, broadly refers to a monovalent hydrocarbon group in which the valency is derived by abstraction of hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 24 carbon atoms. A hydrocarbyl may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal reactive and/or latent reactive functionality and/or leaving groups. "Reactive" functionality refers to functionality which is reactive with common monomer/polymer functionality under normal conditions well understood by those persons of ordinary skill in the relevant art. As non-limiting examples of reactive functionality may be mentioned active hydrogen-containing groups such as hydroxyl, amino, carboxyl, thio, amido, carbamoyl and activated methylene; isocyanato; cyano; epoxy; ethylenically unsaturated groups such as allyl and methallyl; and activated unsaturated groups such acryloyl and methacryloyl, and maleate and maleimido (including the Diels-Alder adducts thereof with dienes such as butadiene). "Latent reactive" functionality within the meaning of the present invention and, as would clearly be understood by those persons of ordinary skill in the art, refers to reactive functionality which is blocked or masked to prevent premature reaction. As examples of latent reactive functionality may be mentioned ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention, as would clearly be understood by those persons of ordinary skill in the relevant art, is a substituent attached to the hydrocarbyl chain or ring which during reaction is dislodged or displaced to create a valency on a carbon or heteroatom in the hydrocarbyl chain or ring, said valency being filled by a nucleophile. As examples of leaving groups may be mentioned halogen atoms such as chlorine, bromine and iodine; hydroxyl groups (protonated and unprotonated); quaternary ammonium salts ($NT_4^+$); sulfonium salts ($ST_3^+$); and sulfonates (—$OSO_3T$); where T is, e.g., methyl or para-tolyl. Of all these classes of reactive functionality, the preferred functionality includes hydroxyl, —$COOR^{50}$, —$CR^5$=$CH_2$, —CO—$CR^{51}$=$CH_2$, Cl, an isocyanate group, a blocked isocyanate group and —$NHR^{50}$, where $R^{50}$ is selected from hydrogen and a hydrocarbyl (preferably of up to 24 carbon atoms); and $R^{51}$ is selected from hydrogen and an alkyl of 1 to 4 carbon atoms (preferably hydrogen and methyl).

The term "hydrocarbylene" in the context of the present invention is a divalent hydrocarbon group in which both valencies derive by abstraction of hydrogens from carbon atoms. Included within the definition of hydrocarbylene are the same groups as indicated above for hydrocarbyl and functional hydrocarbyl with, of course, the extra valency (for example, alkylene, alkenylene, arylene, etc.).

The term "functional hydrocarbylene" in the context of the present invention refers to a species of hydrocarbylene possessing pendant reactive functionality, latent reactive functionality and/or leaving groups. The term "non-functional hydrocarbylene" in the context of the present invention refers generally to a hydrocarbylene other than a functional hydrocarbylene.

The triazines in accordance with the present invention also relate to latent stabilizing compounds against actinic radiation where at least one of the hydroxyl groups on an aryl ring ortho to the point of attachment to the triazine is blocked, that is, wherein at least one X is other than hydrogen. Such latent stabilizing compounds liberate the effective stabilizers by cleavage of the O—X bond, e.g., by heating or by exposure to UV radiation. Latent stabilizing compounds are desirable because they have many favorable properties, i.e., good substrate compatibility, good color properties, a high cleavage rate of the O—X bond and a long shelf life. The use of latent stabilizing compounds is further described in U.S. Pat. Nos. 4,775,707; 5,030,731; 5,563,224 and 5,597,854, which are incorporated herein for all purposes as if fully set forth.

Latent stabilizing compounds comprising the triazines of the present invention can be prepared from compounds when at least one X is hydrogen, by subjecting said compounds to a further reaction to form latent stabilizing compounds, as described in the immediately preceding incorporated references.

As preferred examples of blocking groups X may be mentioned one or more of the following groups: allyl, —$COR^a$, —$SO_2R^b$, —$SiR^cR^dR^e$, —$PR^fR^g$ or —$POR^fR^g$, —$CONHR^h$, wherein each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;

each $R^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each $R^h$ is independently selected from $C_1$–$C_8$ alkyl, $C_5$–$C_{12}$ cycloalkyl, $C_2$–$C_8$ alkenyl, —$CH_2$—CO—$CH_3$, and phenyl which is unsubstituted or substituted by $C_1$–$C_{12}$ alkyl, $C_2$–$C_8$ alkenyl, $C_1$–$C_4$ alkoxy, halogen and/or benzyl.

The reaction to give the latent stabilizing compounds of the present invention in which X is allyl, —$COR^a$, —$SO_2R^b$, —$SiR^cR^dR^e$, —$PR^fR^g$ or —$POR^fR^9$, can be carried out, for example, by reaction of the compounds of the present invention when at least one X is hydrogen with the corresponding halides such as allyl chloride, Cl—$COR^a$, Cl—$SO_2R^b$, Cl—$SiR^cR^dR^e$, Cl—$PR^fR^g$, or Cl—$POR^fR^g$. The reaction to give the latent stabilizing compounds of the present invention in which X is —$CONHR^h$ can be carried out, for example, by reaction of the compounds when at least one X is hydrogen with the corresponding isocyanates. Furthermore, acylated compounds can be obtained by reaction with anhydrides, ketenes or esters, such as lower alkyl esters, as is well known to one skilled in the art. The above-described reagents may be used in approximately equimolar amounts or in excess, for example, from 2 to 20 mol with respect to the hydroxyl groups desired to be made latent in the starting compound.

Catalysts customarily used for acylation, sulfonylation, phosphonylation, silylation or urethanation reactions may be used in forming the latent stabilizing triazines of the present invention. For example, acylation and sulfonylation reaction catalysts such as tertiary or quaternary amines, such as triethylamine, dimethylaminopyridine or tetrabutylammonium salts, may be used for forming these latent stabilizing compounds.

The reaction may be carried out in the presence of a solvent, such as relatively inert organics, e.g., hydrocarbons such as toluene and xylene, chlorinated hydrocarbons such as carbon tetrachloride or chloroform, or ethers such as tetrahydrofuran or dibutyl ether, or without a solvent. Alternatively, the reagent(s) may be employed as the solvent. The reaction temperature is usually between room temperature and about 150° C., for example, up to the boiling point of the solvent when a solvent is used.

In preferred embodiments, each X is hydrogen.

In preferred embodiments, L is selected from the group consisting of hydrogen, $C_1$–$C_{24}$ alkyl or mixtures thereof; $C_1$–$C_{24}$ branched alkyl or mixtures thereof; $C_3$–$C_6$ alkenyl; —COR$^{12}$; —COOR$^{12}$; —CONHR$^{12}$; —SO$_2$R$^{13}$; $C_1$–$C_{18}$ alkyl which is substituted with one or more of the groups: hydroxy, $C_1$–$C_{18}$ alkoxy, $C_3$–$C_{18}$ alkenoxy, halogen, phenoxy, $C_1$–$C_{18}$ alkyl-substituted phenoxy, $C_1$–$C_{18}$ alkoxy-substituted phenoxy, halogen-substituted phenoxy, —COOH, —COOR$^8$, —CONH$_2$, —CONHR$^9$, —CON(R$^9$)(R$^{10}$), —NH$_2$, —NHR$^9$, —N(R$^9$)(R$^{10}$), —NHCOR$^{11}$, —N(R$^9$)COR$^{11}$, —NHCOOR$^{11}$, —N(R$^9$)COOR$^{11}$, —CN, —OCOR$^{11}$, —OC(O)NHR$^9$, —OC(O)NHR$^9$, —OC(O)N(R$^9$)(R$^{10}$); $C_2$–$C_{50}$ alkyl which is interrupted by one or more oxygen atoms or carbonyl groups and optionally substituted by one or more substituents selected from the group consisting of hydroxy, $C_1$–$C_{12}$ alkoxy, and glycidyloxy; glycidyl; and cyclohexyl optionally substituted with hydroxyl or —OCOR$^{11}$.

R$^9$ and R$^{10}$ independently of one another are $C_1$–$C_{12}$ alkyl, $C_3$–$C_{12}$ alkoxyalkyl, $C_4$–$C_{16}$ dialkylaminoalkyl, or $C_5$–$C_{12}$ cycloalkyl, or R$^9$ and R$^{10}$ taken together are $C_3$–$C_9$ alkylene or $C_3$–$C_9$ oxoalkylene or $C_3$–$C_9$ azaalkylene.

R$^{11}$ is a hydrogen or a hydrocarbyl of 1 to 18 carbon atoms which may optionally be substituted by hydroxyl or alkoxy of 1 to 4 carbon atoms and/or contain one or more oxygen and/or nitrogen atoms in the chain.

R$^{12}$ is hydrogen or an alkyl of 1 to 4 carbon atoms.

R$^{13}$ is hydrogen, a hydrocarbyl group of 1 to 8 carbon atoms phenyl.

Some of these groups as well as others are described in U.S. Pat. Nos. 5,106,891; 5,189,084; 5,356,995; 5,637,706; 5,726,309, EP 434,608; EP 704,437; WO 96/28431 and GB 2,293,823 which are incorporated herein by reference for all purposes as if fully set forth.

L may also be an alkyl of 1–24 carbon atoms substituted by a hindered amine light stabilizer (HALS) group of the general Formula XI. Triazines containing tetramethylpiperidine groups are described in U.S. Pat. Nos. 4,161,592 and 5,376,710, which are hereby incorporated by reference herein as if fully set forth.

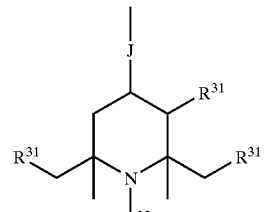

(XIa)

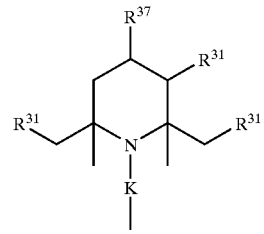

(XIb)

wherein

J is —O—, —NR$^{30}$—, —T—(CH2)2—NR$^{30}$— wherein T is —O— or —S—, and R$^{30}$ is $C_1$–$C_{12}$ alkyl or hydrogen;

R$^{31}$ is hydrogen or $C_1$–$C_8$ alkyl;

R$^{32}$ is hydrogen, oxygen, $C_1$–$C_{21}$ alkoxyalkyl, $C_7$–$C_8$ aralkyl, 2,3-epoxypropyl, and aliphatic acyl group with 1–4 C atoms or one of the groups —CH$_2$COOR$^{33}$, —CH$_2$—CH(R$^{34}$)—OR$^{35}$, —COOR$^{36}$ or —CONHR$^{36}$, wherein R$^{33}$ is $C_1$–$C_{12}$ alkyl, $C_3$–$C_6$ alkenyl, phenyl, $C_7$–$C_8$ aralkyl or cyclohexyl, R$^{34}$ is a hydrogen, methyl or phenyl, R$^{35}$ is hydrogen, an aliphatic, aromatic, aralphatic or alicyclic acyl group with 1–8 C atoms, wherein the aromatic part is unsubstituted or is substituted by chlorine, $C_1$–$C_4$ alkyl, $C_1$–$C_8$ alkoxy or by hydroxyl, and R$^{36}$ is $C_1$–$C_{12}$ alkyl, cyclohexyl, phenyl or benzyl;

R$^{37}$ is hydrogen, —OH or one of the groups —O—CO—R$^{38}$ or —NR$^{36}$—CO—R$^{38}$, wherein R$^{38}$ is $C_1$–$C_{12}$ alkyl or phenyl; and K is —O—(C$_{mm}$H$_{2mm}$)— wherein mm is 1 to 6, Preferred among the sterically hindered amines are members of the group consisting of: bis(2,2,6,6-tetramethylpiperidin-4-yl) sebacate; bis(1,2,2,6,6-pentamethylpiperidin-4-yl)sebacate; bis(1-octyloxy-2,2,6,6-tetramethylpiperidin-4-yl)sebacate; the condensate of N,N'-bis(2,2,6,6-tetramethylpiperidin-4-yl) hexamethylenediamine and 4-tert-octylamino-2,6-dichloro-1,3,5-triazine; the condensate of N,N'-bis(2,2,6,6-tetramethylpiperidin-4-yl)hexamethylenediamine and 4-morpholino-2,6-dichloro-1,3,5-triazine; 3-dodecyl-1-(2,2,6,6-tetramethylpiperidin-4-yl)pyrrolidin-2,5-dione; 3-dodecyl-1-(1-acetyl-2,2,6,6-tetramethylpiperidin-4-yl) pyrrolidin-2,5-dione; a mixture of 4-hexadecyloxy- and 4-stearyloxy-2,2,6,6-tetramethylpiperidine, and mixtures thereof.

Most preferably, each L group is independently selected from hydrogen, an alkyl of 1 to 24 carbon atoms, or mixtures thereof; an alkyl of 4 to 20 carbon atoms containing one or more oxygen atoms in the chain and optionally substituted with one or more hydroxyl groups, or mixtures thereof.

Each of R$_6$ and R$_7$ is independently selected from hydrogen, a hydrocarbyl group of 1 to 24 carbon atoms, a hydrocarbyloxy group of 1 to 24 carbon atoms, an acyl group of 2 to 24 carbon atoms and an acyloxy group of 2 to 24 carbon atoms.

In preferred embodiments, each of $R_6$ and $R_7$ is independently selected from hydrogen, halogen, an acyl of 2 to 24 carbon atoms, benzoyl, alkyl of 1 to 24 carbon atoms, an alkenyl of 2 to 24 carbon atoms, a cycloalkyl of 5 to 24 carbon atoms; and an aralkyl of 7 to 24 carbon atoms.

Another preferred embodiment is when $R_1$ to $R_7$ and X is hydrogen, T' is oxygen and Y is hydrogen or a $C_1$ to $C_8$ alkyl.

In yet another embodiment, $R_6$ and $R_7$ are independently methylene, alkylidene, or benzylidene substituted by a benzophenone UV absorber or a benzotriazole UV absorber. Related triazine-benzotriazole and triazine-benzophenone hybrid UV absorbers are disclosed in U.S. Pat. No. 5,585,422 which is incorporated by reference herein for all purposes fully set forth. In a related preferred embodiment, $R_6$ and $R_7$ are independently methylene, alkylidene, or benzylidene substituted by a second triazine UV absorber. Related triazine dimers (and oligomers) are disclosed in U.S. Pat. No. 5,726,309 and EP 704,437, which are incorporated by reference herein for all purposes fully set forth.

Preferred benzotriazoles comprise at least one member of the group consisting of: 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol]; the transesterification product of 2-[3'-tert-butyl-5'-methoxycarbonylethyl)-2'-hydroxyphenyl]benzotriazole with polyethylene glycol 300; [R—CH$_2$CH—COO(CH$_2$)$_3$]$_2$— where R=3'-tert-butyl-4'-hydroxy-5'-2H-benzotriazol-2-ylphenyl; and derivatives thereof. Most preferred benzotriazoles are members of the group consisting of: 2-(2'-hydroxy-5'-(1,1,3,3-tetramethylbutyl)phenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; 2-(3'-tert-butyl-2'-hydroxy-5'-(2-octyloxycarbonylethyl)phenyl) benzotriazole, the transesterification product of 2-[3'-tert-butyl-5'-(2-methoxycarbonylethyl)-2'-hydroxyphenyl] benzotriazole with polyethylene glycol 300 and mixtures thereof.

In preferred embodiments, $R^{11}$ is a hydrogen or a hydrocarbyl of 1 to 18 carbon atoms which may optionally be substituted by hydroxyl or alkoxy of 1 to 4 carbon atoms and/or contain one or more oxygen and/or nitrogen atoms in the chain. More preferably, $R^{11}$ is selected from hydrogen and hydrocarbyl of 1 to 18 carbon atoms, which may optionally be substituted by hydroxyl or alkoxy of 1 to 4 carbon atoms.

In preferred embodiments, $R^{12}$ is selected from hydrogen and an alkyl of 1 to 4 carbon atoms. More preferably, $R^{12}$ is selected from hydrogen and a methyl group.

In preferred embodiments, $R^{13}$ is selected from hydrogen, a hydrocarbyl group of 1 to 8 carbon atoms, or phenyl. More preferably, $R^{13}$ is hydrogen or methyl.

Further preferred embodiments may include any combination of the parameters mentioned above.

Methods of Preparation

The method of preparing the novel triazines of the present invention can be preformed by any suitable method as mentioned above. Preferably, the method of producing the novel triazine compound is from the method described in WO 00/29392 herein incorporated by reference in its entirety.

The term "Lewis acid" is intended to include aluminum halides, alkylaluminum halides, boron halides, tin halides, titanium halides, lead halides, zinc halides, iron halides, gallium halides, arsenic halide, copper halides, cadmium halides, mercury halides, antimony halides, and the like. Preferred Lewis acids include aluminum trichloride, aluminum tribromide, trimethylaluminum, boron trifluoride, boron trichloride, zinc dichloride, titanium tetrachloride, tin dichloride, tin tetrachloride, or a mixture thereof.

As used herein the term "reaction promoter" is understood to comprise a compound, which is used in combination with the Lewis acid to facilitate the reaction. Suitable reaction promoters include acids, bases, water, alcohols, aliphatic halides, halide salts, acid halides, halogens, alkenes, alkynes, ester, anhydride, carbonate, urethane, carbonyl, epoxy, ether, acetal compounds, or mixtures thereof. For a more detailed list of reaction promoters, refer to WO 00/29392.

The novel triazines of the present invention can be prepared through the modified Friedel-Crafts reaction of a cyanuric halide with a phenyl ether in the presence of a reaction promoter and a Lewis acid, (see Scheme 1), followed by or reacted concurrently with a resorcinol-based phenolic compound.

Scheme 1

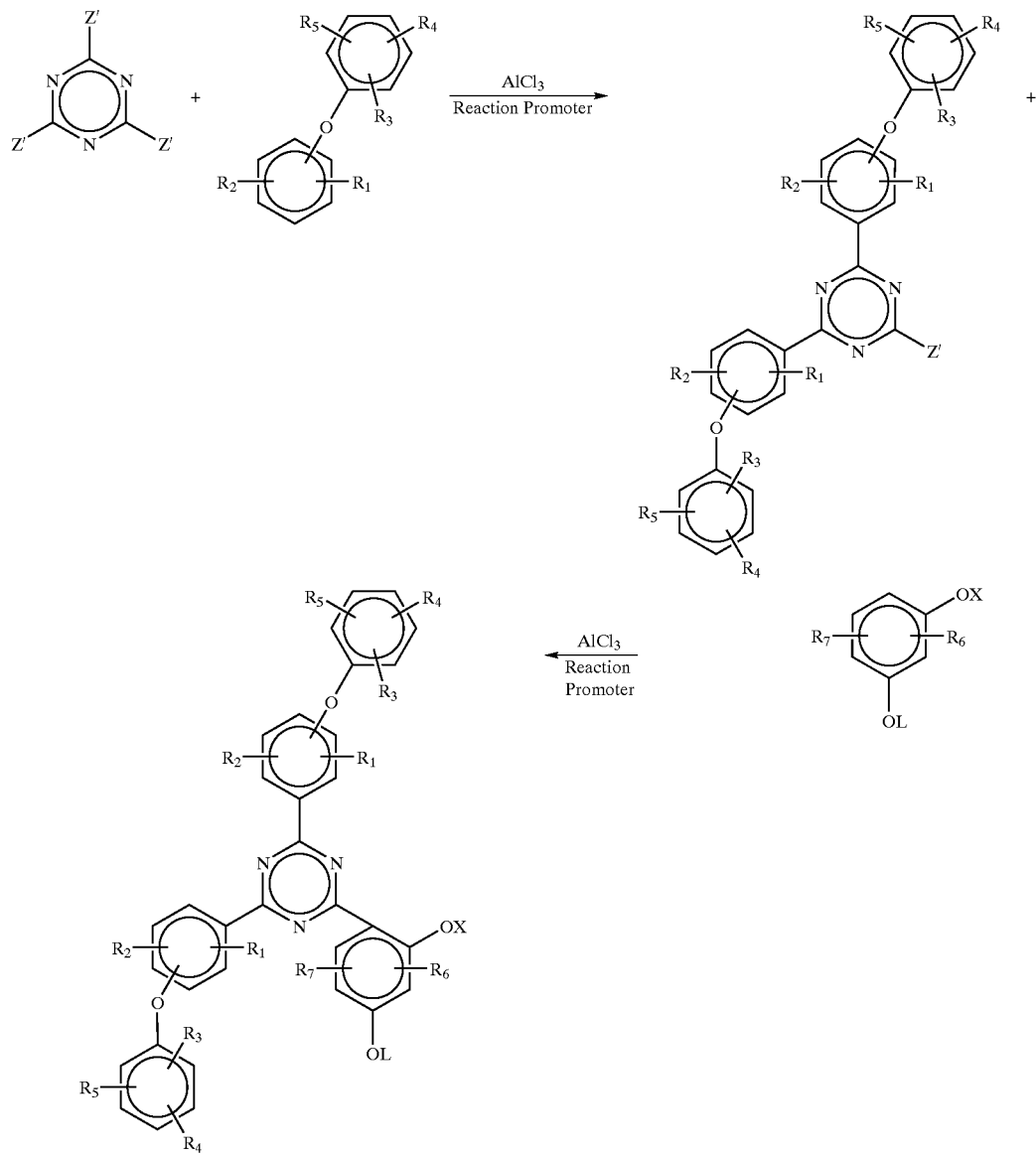

wherein Z' is fluorine, bromine, chlorine, or iodine and the other substituents are defined above.

The relative amounts of the reactants are as follows. The amount of phenyl ether compound should be in sufficient amounts to react with the cyanuric halide to produce the desired intermediate compound. If a mono-phenyl ether triazine compound is desired, then about 1 molar equivalents should be reacted with the cyanuric halide. If a bis(phenyl ether) triazine compound is desired, then about 2 molar equivalents of phenyl ether should be reacted with the cyanuric halide. It should be noted that other embodiments of the present invention are the mono-phenyl ether and bis(phenyl ether) triazine intermediate compounds.

The amount of Lewis acid, such as $AlCl_3$, used in the reaction should be in sufficient amounts to transform the cyanuric halide to the desired intermediate and/or end product. The amount of Lewis acid should be between about 0.5 to about 500 mol equivalents to the cyanuric halide.

Preferably, the amount of Lewis acid should be between about 1 to about 5 mol equivalents to the cyanuric halide or about 2 to about 4 mol equivalents to cyanuric halide. The preferred Lewis acid is aluminum trichloride.

Advantageously, a reaction promoter can be used in conjunction with a Lewis acid when synthesizing the desired compounds. Preferably, the amount of reaction promoter should be between about 0.01 mol to about 5 mol equivalents, or about 0.1 mol to about 2 mol equivalents.

The reaction should run for a sufficient amount of time, at a sufficient temperature and pressure to synthesize the desired triazine. The preferred reaction time for the synthesis of the intermediate compound, i.e., the first step, is between about 5 minutes and about 48 hours, more preferred between about 15 minutes and about 24 hours. The preferred reaction time for the synthesis of end product compound, i.e., the second step, is between about 10 minutes and about 24 hours, more preferably time is between about 30 minutes and about 12 hours. The preferred reaction temperature for the first step is between about −50° C. and about 150° C., more preferred reaction temperature between about −30° C. and about 50° C. The reaction pressure is not critical and can be about 1 atmosphere or higher if desired. Preferably, the reaction is carried out under an inert gas such as nitrogen or argon. The preferred reaction temperature for the second step is between about 0° C. and about 120° C., a more preferred reaction temperature is between about 20° C. and about 100° C.

The step-wise process comprises mixing at least one Lewis acid, at least one reaction promoter, cyanuric halide and phenyl ether, preferably until the reaction is between about 70% to about 100% completed. Thereafter, the product is isolated and purified. The intermediate product is then added to the subsequent reactant along with Lewis acid and optionally a reaction promoter to synthesize the desired end product. The step-wise sequence allows for the isolation, purification, and storage of compounds of the intermediate prior to subsequent reaction with phenol-based compounds, such as resorcinol.

The continuous reaction comprises allowing the cyanuric halide to react with one or more phenyl ethers in the presence of at least one Lewis acid and at least one a reaction promoter preferably until the reaction is between about 70% to about 100% complete. Thereafter, without isolating the intermediate product, the resorcinol-based phenolic compound is allowed to react with the intermediate product in the presence of optionally at least one second Lewis acid and optionally at least one second reaction promoter preferably until the reaction is between about 70% to about 100% complete. The continuous reaction eliminates the need to purify the intermediate product or use of additional reagents such as solvents, and optionally Lewis acids and acids. Moreover, the one-step process simplifies the synthetic reaction pathway such that no unnecessary handling or processing of the reaction mixture is required until the reaction is completed.

In an another process as disclosed in U.S. Pat. No. 6,225,468 B1 cyanuric chloride can be simultaneously reacted with phenyl ether and resorcinol in the presence of Lewis acid, such as aluminum chloride, to obtain the desired product.

Uses of the Triazines

As indicated earlier, the novel triazines of the present invention are particularly useful as ultraviolet light absorber agents for stabilizing a wide variety of materials including, for example, various polymers (both cross-linked and thermoplastic), photographic materials and dye solutions for textile materials, as well as in ultraviolet light screening agents (such as sunscreens). The novel triazines of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the triazines of the present invention can be employed to stabilize materials which are subject to degradation by ultraviolet radiation by incorporating the presently claimed compounds into a composition comprising polymeric materials, either chemically or physically. Non-limiting examples of polymeric materials that may be so stabilized are polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, SAN (styrene acrylonitrile), ASA (acrylate styrene acrylonitrile), cellulosic acetate butyrate, cellulosic polymers, polyimides, polyamideimides, polyetherimides, polyphenylsulfides, PPO, polysulfones, polyethersulfones, polyvinylchlorides, polycarbonates, polyketones, aliphatic polyketones, thermoplastic TPO's, aminoresin cross-linked polyacrylates and polyesters, polyisocyanate cross-linked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and blends thereof.

The preferred polymeric material is selected from the group consisting of polyolefins; copolymers of one or more monoolefins and/or diolefins with carbon monoxide and/or with other vinyl monomers; hydrocarbon resins (such as $C_5$–$C_9$) including hydrogenated modifications thereof and mixtures of polyalkylenes and starch; polyesters; copolyethers esters; polyethers; polyketones; polyamides and copolyamides derived from diamines, dicarboxylic acids and/or aminocarboxylic acids or the corresponding lactams; natural and synthetic rubbers and elastomers; polyurethanes; polystyrenes, poly-α-methylstyrenes and copolymers with other vinyl monomers; graft copolymers of styrene; high impact polystyrenes; polyacrylic acids, polymethacrylics acids, polyacrylates, polymethacrylates, polyacrylamides, polyacrylonitriles; homo- and copolymers derived from unsaturated alcohols and amines or the acyl derivatives or acetals thereof such as polyvinyl alcohol, polyvinyl acetate, polyacetals, and polybutyrals; homo- and copolymers of cyclic ethers such as alkylene glycols and alkylene oxides, as well as copolymers with bisglycidyl ethers; polybutadienes; polystyrenes; ABS (acrylonitrile butadiene styrene); SAN (styrene acrylonitrile); ASA (acrylate styrene acrylonitrile); cellulosic acetate butyrate; cellulosic polymers; polyureas; polyimides; polyamides-imides; polyesterimides; polyether-imides; polyhydantoins; polybenzimidazoles; polyphenylsulfide; PPO (polypropylene oxide); polysulfones; polyether sulfones; polyether ketones; halogen-containing polymers; polyvinylchlorides; polycarbonates; polyester carbonates; thermoplastic TPO's; amino resin cross-linked polyacrylates and polyesters; polyisocyante cross-linked polyesters and polyacrylates; phenol/formaldehyde, urea/formaldehyde and melamine/formaldehyde resins; saturated and unsaturated polyester resins; cross-linkable acrylic resins derived from substituted acrylates such as epoxy acrylates, hydroxy acrylates, isocyanato acrylates, urethane acrylates or polyester acrylates; alkyd resins, polyester resins, and acrylate resins cross-linked with melamine resins, urea resins, isocyanates, isocyanurates, carbamates, or epoxy resins; cross-linked epoxy resins derived from aliphatic cycloaliphatic, heterocyclic and/or aromatic glycidyl compounds which are cross-linked with anhydrides or amines; polysiloxanes; Michael addition polymers of amines or blocked amines (e.g., ketimines) with activated unsaturated and/or methylene compounds; of ketimines with activated unsaturated and/or methylene compounds such as acrylates and methacrylates, maleates, and acetoacetates; polyketimines in combination with unsaturated acrylic polyacetoacetate resins or with unsaturated acrylic resins; radiation curable compositions; epoxymelamine resins; natural polymers such as cellulose, rubber, gelatin, and chemically modified derivatives thereof; organic dyes and pigments; any mixture or blends of the above; cosmetic products; cellulose-based paper formulations; photographic film; paper; ink; and intraocular lenses.

Depending upon their ultimate end use, the triazines of the present invention may be combined with a variety of additives conventionally employed in the UV stabilizing art such as anti-oxidants, UV absorbers and stabilizers, metal deactivators, phosphites and phosphonites, hydroxylamines, nitrones, thiosynergists, co-stabilizers, nucleating agents, fillers and reinforcing agents, plasticizers, lubricants, emulsifiers, pigments, rheological additives, catalysts, level agents, optical brighteners, flameproofing agents, anti-static agents and blowing agents. Examples of these additives may be found, for example, in U.S. Pat. No. 6,096,886, herein incorporated by reference in its entirety. Further examples are those described in many of the previously incorporated references as well as Ullmann's Encyclopedia of Industrial Chemistry, 5th Edition, Vol. A18, pp. 429–471, VCH, Weinheim 1991; and Calbo, Leonard J., ed., Handbook of Coatings Additives, New York:Marcel Dekker (1987).

Especially preferred are other UV stabilizers and anti-oxidants including, but not limited to 2-(2'-hydroxyphenyl) benzotriazoles, oxamides, 2-(2-hydroxphenyl)-1,3,5-triazines, 2-hydroxybenzophenones, sterically hindered amines and hindered phenol antioxidants.

Examples of such anti-oxidants and UV stabilizers are: 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl) benzotriazole; 2-(3',5'-di-tert-amyl-2'-hydroxphenyl) benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'hydroxy-5'-methylphenyl)benzotriazole and 2-(3'-tert-butyl-2'-hydroxy-5'-(2-isooctyloxycarbonylethyl) phenylbenzotriazole; 2,2-methylenebis[4-(1,1,3,3-tetramethylbutyl)-6-benzotriazol-2-ylphenol], the transesterification product of 2-[3'-tert-butyl-5'-(2-methoxycarbonylethyl)-2'-hydroxyphenyl]benzotriazole with polyethylene glycol 300; [R—$CH_2CH$—$COO(CH_2)_3]_2$ B where R=3'-tert-butyl-4'-hydroxy-5'-2H-benzotriazol-2-ylphenyl; bis(2,2,6,6-tetramethylpiperidin-4-yl)sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpeperidine; 4-stearyloxy-2,2,6,6-tetramethylpiperidine; bis(1,2,2,6,6-pentamethylpeperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis (2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines and the reaction product of 7,7,9,9-tetramethyl-2-cycloundecyl-1-oxa-3,8-diaza-4-oxospiro[4.5]decane and epichlorohydrin; 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5- triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis (2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy) phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis (2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy) phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; 2-(2-hydroxyphenyl)-4-(4-methoxyphenyl)-6-phenyl-1,3,5triazine, 2,4-dihydroxybenzophenone; 2-hydroxy-4-methoxybenzophenone; 2-hydroxy-4-octyloxybenzophenone; 2-hydroxy-4-decyloxybenzophenone; 2-hydroxy-4-dodecyloxybenzophenone; 2-hydroxy-4-benzyloxybenzophenone, 4,2',4-trishydroxybenzophenone; 2'-hydroxy-4,4'-dimethoxybenzophenone; 1,3,5-tris(2,6-dimethyl-4-tert-butyl-3hydroxybenzyl)isocyanurate; 1,3,5-tris(3,5-di-tert-butyl-4-hydroxybenzyl)isocyanurate; 1,3,5-tris(3,5-di-tert-butyl-4-hydroxybenzyl)-2,4,6-trimethylbenzene; 2,6-di-tert-butyl-4-methylphenol; 2,2'-ethylidene-bis(4,6-di-tert-butylphenol); 1,1,3-tris(5-tert-butyl-4-hydroxy-2-methylphenyl)butane; esters of β-(3,5-di-tert-butyl-4-hydroxyphenyl)propionic acid with mono- or polyhydric alcohols; esters of β-(5-tert-butyl-4-hydroxy-3-methylphenyl)propionic acid with mono- or polyhydric alcohols; dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid; amides of β-(3,5-di-tert-butyl-4-hydroxyphenyl)propionic acid such as N,N'-bis(3,5-di-tert-butyl-4-hydroxyphenylpropionyl) hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

The weight ratio of the triazine compounds of the present invention to the other additives, such as the preferred additives may be, for example from about 500:1 to about 1:500, or about 100:1 to about 1:100, or about 10:1 to about 1:10. The novel triazines of the present invention can also be employed in multilayer systems. In such systems, a polymer composition having from about 0.1 to about 20% by weight and preferably a relatively high content of novel triazine stabilizer, for example, about 5–15% by weight, is applied in a thin film (e.g., about 5–500 μm thick and, preferably, about 10–100 μm thick) to a shaped article made from a polymer containing little or no ultraviolet stabilizers. Such composition may be applied at the same time as the shaping of the base structure, for example by co-extrusion in a manner analogous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to about 20%, preferably about 1 to about 15%, and most preferably about 2 to about 10% by weight of the outer layer composition, of at least one of the triazine compounds of the present invention.

The polymers stabilized in this way are notable for high weathering resistance, especially for high resistance to UV light. This enables them to retain their mechanical properties, and their color surface properties such as gloss and distinctness of image, for a long time even when used outside. Moreover, due to the bondable nature of the presently claimed triazine compounds, migration of these UV absorbers between the layers of the multi-layer coatings can, under the appropriate circumstances, be minimized.

In another embodiment of the present invention, the novel triazine compounds can be used as stabilizers for coatings, for example for paints such as disclosed in numerous references (see, e.g., U.S. Pat. Nos. 4,619,956; 4,740,542; 4,826,978; 4,962,142; 5,106,891; 5,198,498; 5,298,067; 5,322,868; 5,354,794; 5,369,140; 5,420,204; 5,461,151; 5,476,937; EP-0434608 and EP-A-0444323). Of particular interest are coatings and paints for the automobile industry. The invention therefore also relates to those compositions which are film-forming binders for coatings.

Such novel coating compositions comprise about 0.01 to about 20%, preferably about 0.01 to about 10%, and more preferably about 0.02 to about 5% by weight of the binder of the coating composition of the presently claimed triazines of the present invention.

To achieve maximum light stability, it is of particular interest to add sterically hindered amines, examples of which are set out in the above-mentioned section b(vi). The invention therefore also relates to a coating composition which, in addition to the binder, the novel triazines and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

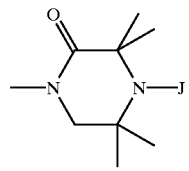

in which J is, for example, hydrogen, hydroxyl, alkyl (such as methyl), alkoxy (such as methoxy) or acyl.

More preferably the stabilizer is a 2,2,6,6-tetraalkylpiperidine derivative containing at least one group of the formula:

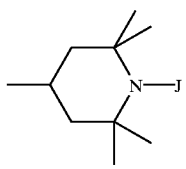

in which J is, for example, hydrogen, hydroxyl, alkyl (such as methyl), alkoxy (such as methoxy) or acyl.

Examples of tetraalkylpiperidine derivatives which can be used in combination with the present trisaryl-1,3,5-triazine compounds are given in U.S. Pat. Nos. 4,314,933; 4,344,876; 4,426,471; 4,426,472; 4,619,956; 5,004,770; 5,006,577; 5,064,883; 5,112,890; 5,124,378; 5,106,891; 5,204,473 and 5,461,151, which are incorporated by reference herein for all purposes as if fully set forth. It is particularly expedient to employ the following tetraalkylpiperidine derivatives, as well as their N-alkyl, N-acyl, N-hydroxyl and N-alkoxy analogs (where not already included in the following list):
bis(2,2,6,6-tetramethylpiperid-4-yl)succinate,
bis(2,2,6,6-tetramethylpiperid-4-yl)sebacate,
bis(1,2,2,6,6-pentamethylpiperid-4-yl)sebacate,
di(1,2,2,6,6-pentamethylpiperid-4-yl)butyl-(3,5-di-tert-butyl-4-hydroxybenzyl)malonate, bis(1-octyloxy-2,2,6,6-tetramethylpiperid-4-yl)sebacate, tetra(2,2,6,6-tetramethylpiperid-4-yl)butane-1,2,3,4-tetracarboxylate, tetra(1,2,2,6,6-pentamethylpiperid-4-yl)butane-1,2,3,4-tetracarboxylate, 2,2,4,4-tetramethyl-7-oxa-3,20-diaza-21-oxo-dispiro[5.1.11.2]heneicosane, and 8-acetyl-3-dodecyl-1,3,8-triaza-7,7,9,9-tetramethylspiro[4.5]decane-2,4-dione.

Commercially available examples of these and other tetraalkylpipieridine derivatives include SANDUVOR® 3050, 3052, 3055, 3056, 3058, PR-31 and PR-32 (Clariant Corp.); TINUVIN® 079L, 123, 144, 292, 440L and 622LD (Ciba Specialty Chemicals); CHIMASORB® 119 and 944 (Ciba Specialty Chemicals); and CYASORB® UV-3346, UV 3529, UV-3853, UV-500 and UV-516 (Cytec Industries Inc.).

The novel coating compositions according to the invention can be applied to any desired substrates, for example to metal, wood, plastic, fiberglass or ceramic materials. The coating compositions can be pigmented mono-coats or multi-layer (primer/basecoat/clearcoat) systems typical of automotive finishes. In the latter case, the novel coating composition can be used for either the base coat, or clear coat, or for both layers. If the topcoat of an automotive finish comprises two layers, of which the lower layer is pigmented and the upper layer is not pigmented, the novel coating composition can be used for either the upper or the lower layer or for both layers, but preferably for the upper topcoat layer.

For more detailed examples of these and other uses for UV stabilizers, such as the triazines of the present invention, see U.S. Ser. No. 09/335,886, filed on Jun. 18, 1999, (WO 99/67226, pages 33 to 81), herein incorporated by reference.

The invention will now be illustrated by the following examples. The examples are not intended to be limiting of the scope of the present invention. In conjunction with the general and detailed descriptions above, the examples provide further understanding of the present invention.

EXAMPLES

Examples and reaction schemes for producing specific examples of phenyl ether substituted triazines in accordance with the invention are provided below. While the following examples illustrate preparations with one or more phenyl ethers, one of ordinary skill will understand that these reactions may also be carried out with any of a variety of other substituted phenyl ethers.

PREPARATIVE EXAMPLES

Example 1

Reaction of Cyanuric Chloride with Phenyl Ether: Preparation of 2-chloro-4,6-(bis(4-phenoxyphenyl)-1,3,5-triazine

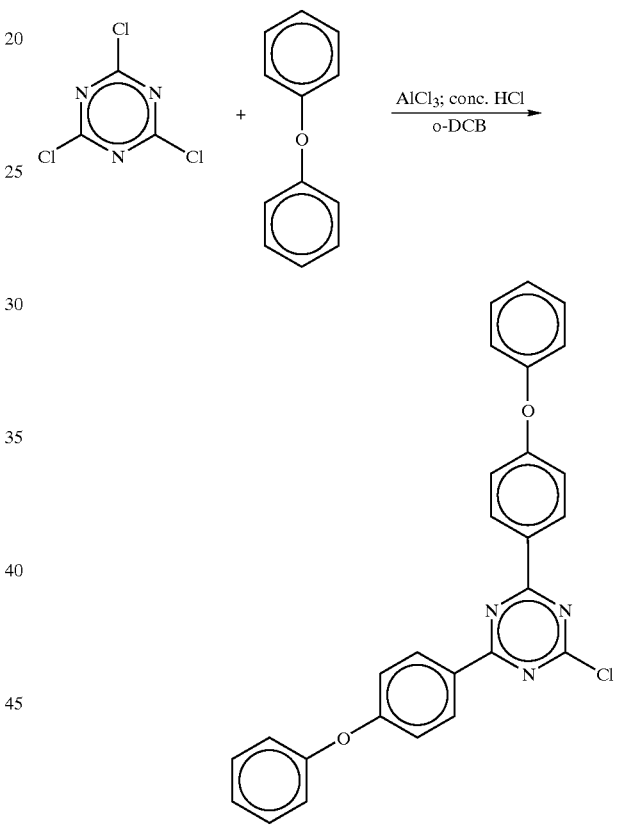

To a stirring mixture of 18.4 gm of cyanuric chloride, 40 gm of aluminum chloride in 250 ml of chlorobenzene cooled in an ice-bath was added 2 ml of conc. HCl. To it was then added 32.3 gm of phenyl ether and the reaction mixture stirred around 0° C. for 6 hr. It was then stirred at room temperature for 18 hr and then quenched with water. The mixture was extracted with methylene chloride, and the organic layer washed with water, and concentrated under reduced pressure. The crude reaction product weighed 44.2 gm which contained 2-chloro-4,6-bis(4-phenoxyphenyl)-1,3,5-triazine.

Almost pure 2-chloro-4,6-bis(4-phenoxyphenyl)-1,3,5-triazine was isolated by column chromatography which was further reacted with resorcinol as discussed in Example 2.

Example 2

Reaction of 2-chloro-4,6-bis(4-phenoxyphenyl)-1,3,5-triazine with Resorcinol: Preparation of 2-(2,4-dihydroxyphenyl)-4,6-bis(4-phenoxyphenyl)-1,3,5-triazine

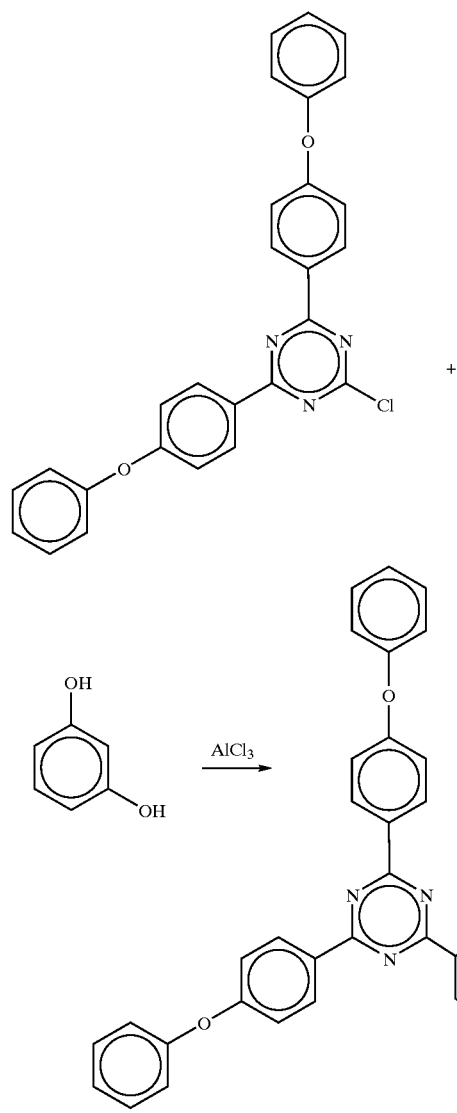

A mixture of 5.9 gm of 2-chloro-4,6-bis(4-phenoxyphenyl)-1,3,5-triazine, 2.6 gm aluminum chloride and 1.6 gm of resorcinol in 25 ml chlorobenzene was heated under nitrogen at 85° C. for 3 hr. An additional 0.17 gm resorcinol was added, and the heating continued for another 1 hr. The reaction mixture was cooled to room temperature, and quenched with water. The precipitated product was filtered, washed with water, and dried to give 5.1 gm of crude 2-(2,4-dihydroxyphenyl)-4,6-bis(4-phenoxyphenyl)-1,3,5-triazine.

Example 3

Preparation of 2-(2,4-dihydroxyphenyl)-4,6-bis(4-phenoxyphenyl)-1,3,5-triazine

To a stirring mixture of 3.7 g of cyanuric chloride, 8 gm of aluminum chloride in 50 ml of chlorobenzene cooled in an ice-bath was added 0.4 ml of conc. HCl. To it was then added 6 ml of phenyl ether, and the reaction mixture stirred around 0° C. for 1 hr. The cooling bath was then removed, and the mixture stirred at room temperature for about 20 hr. At this stage, 2.42 gm of resorcinol was added to the reaction flask, and the contents heated to 80° C. for 3 hr. The heating was discontinued, and the mixture cooled to room temperature. To it was then added 150 ml of cold HCl. The resulting mixture was concentrated under reduced pressure to dryness. The residue was then stirred with 200 ml water for 4 hr at room temperature, the precipitated material filtered, washed with additional water, and dried to give 8.2 gm of crude 2-(2,4-dihydroxyphenyl)-4,6-bis(4-phenoxyphenyl)-1,3,5-triazine.

Example 4

Reaction of 2-(2,4-dihydroxyphenyl)-4,6-bis(4-phenoxyphenyl)-1,3,5-triazine with n-butyl Iodide: Preparation of 2-(2-hydroxy-4-butoxyphenyl)-4,6-bis(4-phenoxyphenyl)-1,3,5-triazine

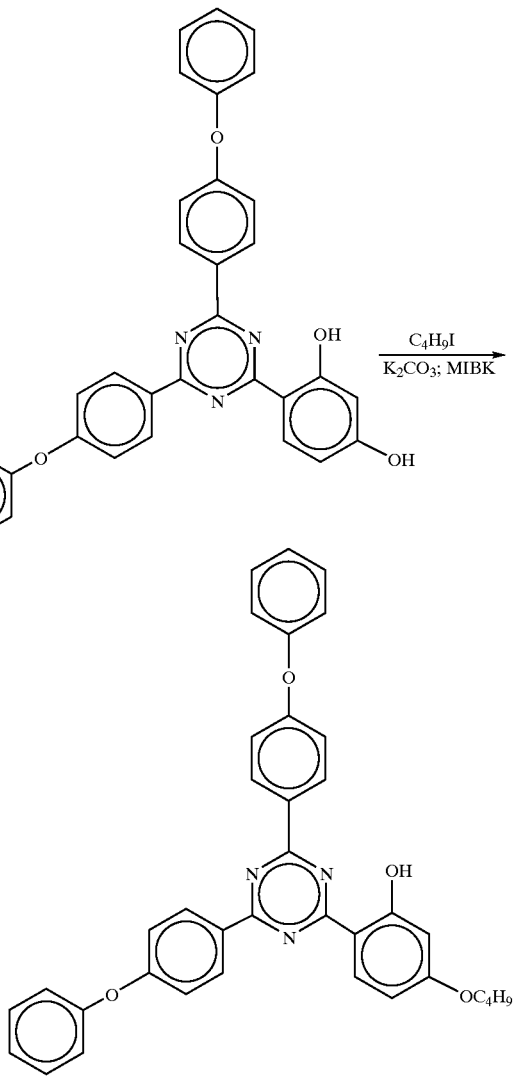

A mixture of 4.5 gm 2-(2,4-dihydroxyphenyl)-4,6-bis(4-phenoxyphenyl)-1,3,5-triazine, 2.02 gm 1-iodobutane, 4.83 gm anhydrous potassium carbonate, 0.25 gm Aliquat 336 and 50 ml acetone was heated to reflux for 7 hr. The reaction mixture was cooled to room temperature, diluted with water and extracted with methylene chloride. The organic layer was washed with water, and concentrated under reduced pressure. The residue thus obtained was analyzed by HPLC and mass spectroscopy to contain the desired 2-(2-hydroxy-4-butyloxyphenyl)-4,6-bis(4-phenoxyphenyl)-1,3,5-triazine.

Example 5

Reaction of 2-(2,4-dihydroxyphenyl)-4,6-bis(4-phenoxyphenyl)-1,3,5-triazine with n-octyl Iodide: Preparation of 2-(2-hydroxy-4-octyloxyphenyl)-4,6-bis(4-phenoxyphenyl)-1,3,5-triazine

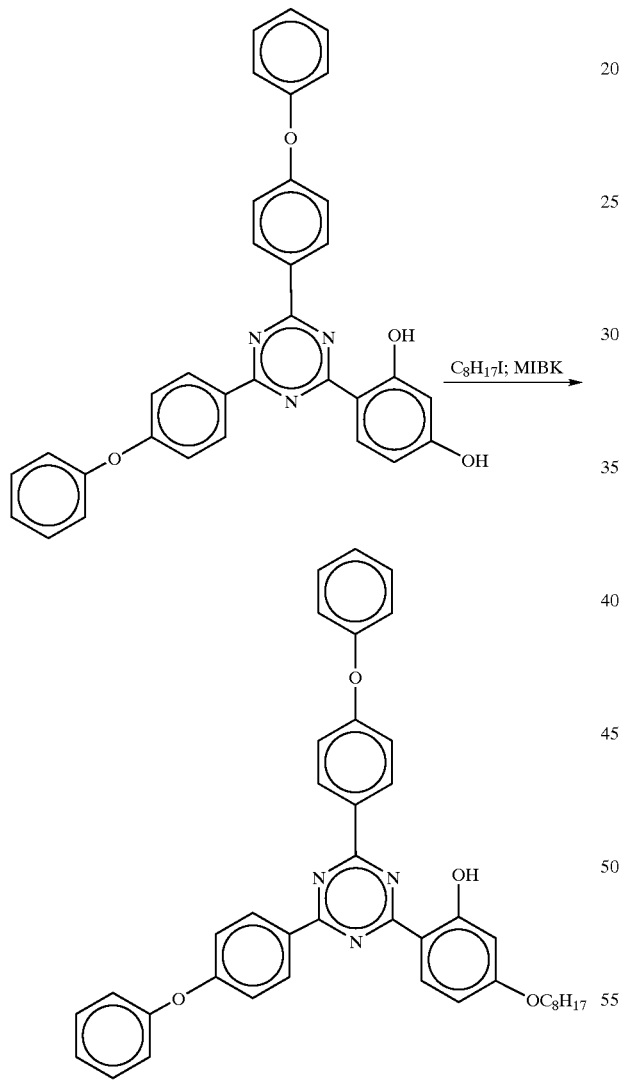

A mixture of 5 gm 2-(2,4-dihydroxyphenyl)-4,6-bis(4-phenoxyphenyl)-1,3,5-triazine, 2.5 gm 1-iodooctane, 6.6 gm anhydrous potassium carbonate, 0.5 gm Aliquat 336 and 25 ml MIBK was heated to reflux for 3 hr. The reaction mixture was cooled to room temperature, diluted with methylene chloride, filtered through Celite. The filtrate was concentrated under reduced pressure. The residue thus obtained was passed through a silica gel column. The material thus obtained was crystallized with acetone to give 3.5 gm of pure 2-(2-hydroxy-4-octyloxyphenyl)-4,6-bis(4-phenoxyphenyl)-1,3,5-triazine.

Example 6

Reaction of 2-(2,4-dihydroxyphenyl)-4,6-bis(4-phenoxyphenyl)-1,3,5-triazine with Ethyl Chloroacetate

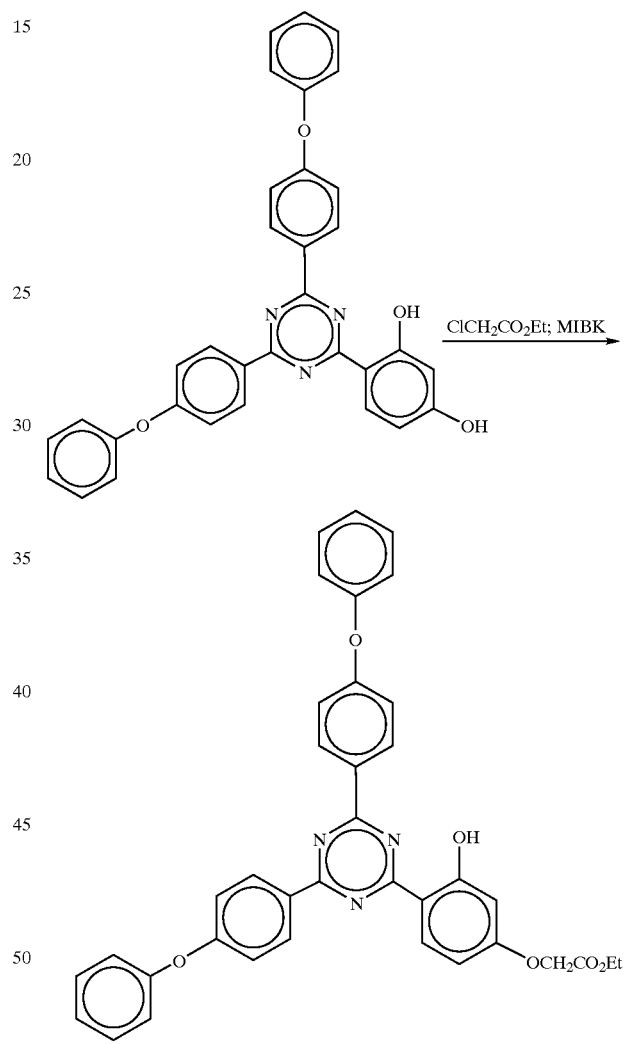

To a stirring mixture of 4.5 gm of 2-(2,4-dihydroxyphenyl)-4,6-bis(4-phenoxyphenyl)-1,3,5-triazine, 4.83 gm of potassium carbonate, 0.25 gm of Aliquat 336 and 50 ml acetone was added 1.35 gm of ethyl chloroacetate. The reaction mixture was heated to reflux under nitrogen for 7 hr. It was cooled to room temperature, diluted with water, and extracted with methylene chloride. The methylene chloride extract was washed with water, dried, and concentrated under reduced pressure to give 3 gm of crude derivative analyzed based on HPLC and mass spectroscopy.

Example 7

Reaction of 2-(2,4-dihydroxyphenyl)-4,6-bis(4-phenoxyphenyl)-1,3,5-triazine with 2,4-dimethyl-3-chloromethyl-6-tert.butylphenol

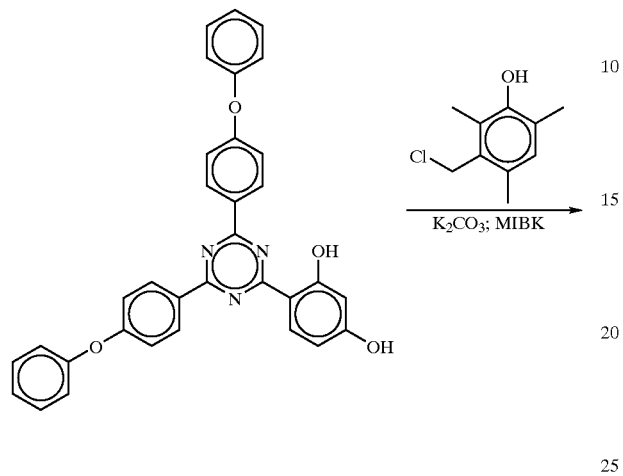

Example 8

Reaction of 2-(2,4-dihydroxyphenyl)-4,6-bis(4-phenoxyphenyl)-1,3,5-triazine with Benzoyl Chloride

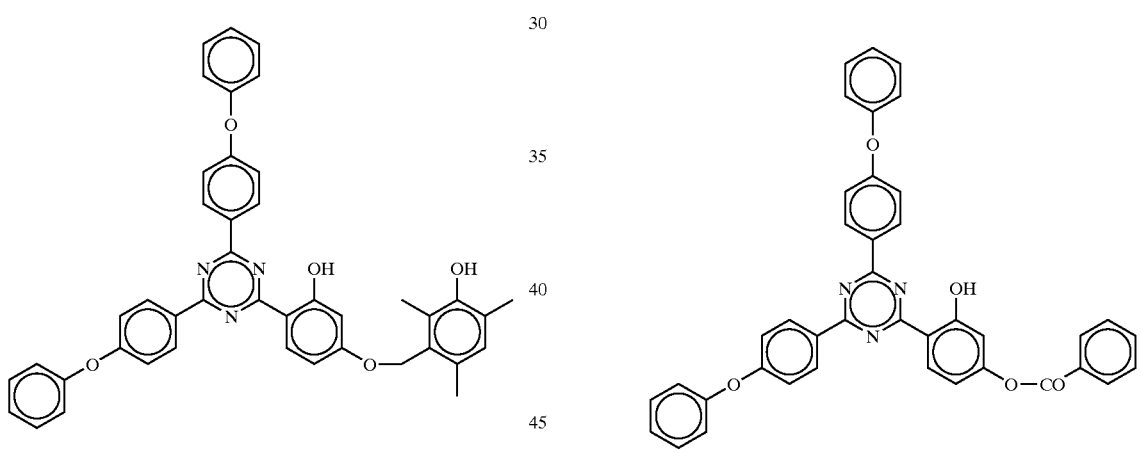

To a stirring mixture of 5.3 gm of 2-(2,4-dihydroxyphenyl)-4,6-bis(4-phenoxyphenyl)-1,3,5-triazine, 4.1 gm of potassium carbonate, 0.25 gm of Aliquat 336 and 25 ml MIBK was added 2.3 gm of 2,4-dimethyl-3-chloromethyl-6-tert.butylphenol. The reaction mixture was heated to reflux under nitrogen for 2 hr. It was cooled to room temperature, diluted with water, and extracted with methylene chloride. The methylene chloride extract was washed with water, dried, and concentrated under reduced pressure to give 4.5 gm of a crude product analyzed based on HPLC and mass spectroscopy to contain the desired product.

To a stirring mixture of 4.5 gm of 2-(2,4-dihydroxyphenyl)-4,6-bis(4-phenoxyphenyl)-1,3,5-triazine, 4.83 gm of potassium carbonate, 0.5 gm of Aliquat 336 and 50 ml acetone was added 1.41 gm of benzoyl chloride. The reaction mixture was heated to reflux under nitrogen for 6 hr. It was cooled to room temperature, diluted with water, and extracted with methylene chloride. The methylene chloride extract was washed with water, dried, and concentrated under reduced pressure to give 1.8 gm of crude benzoate derivative, analyzed based on HPLC and mass spectroscopy.

Example 9

Reaction of 2-(2,4-dihydroxyphenyl)-4,6-bis(4-phenoxyphenyl)-1,3,5-triazine with Benzenesulfonyl Chloride

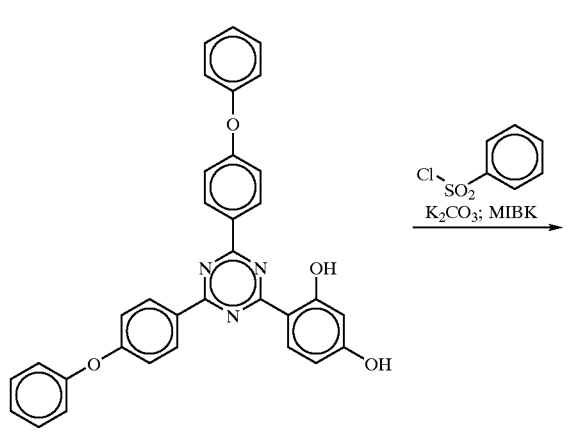

To a stirring mixture of 4.5 gm of 2-(2,4-dihydroxyphenyl)-4,6-bis(4-phenoxyphenyl)-1,3,5-triazine, 4.8 gm of potassium carbonate, 0.5 gm of Aliquat 336 and 50 ml acetone was added 1.8 gm of benzenesulfonyl chloride. The reaction mixture was heated to reflux under nitrogen for 6 hr. It was cooled to room temperature, diluted with water, and extracted with methylene chloride. The methylene chloride extract was washed with water, dried, and concentrated under reduced pressure to give 3.4 gm of crude sulfonate derivative analyzed based on HPLC and mass spectroscopy.

Example 10

Reaction of 2-chloro-4,6-bis(4-phenoxyphenyl)-1,3,5-triazine with Resorcinol: Preparation of 2-(2,4-dihydroxy-6-methylphenyl)-4,6-bis(4-phenoxyphenyl)-1,3,5-triazine

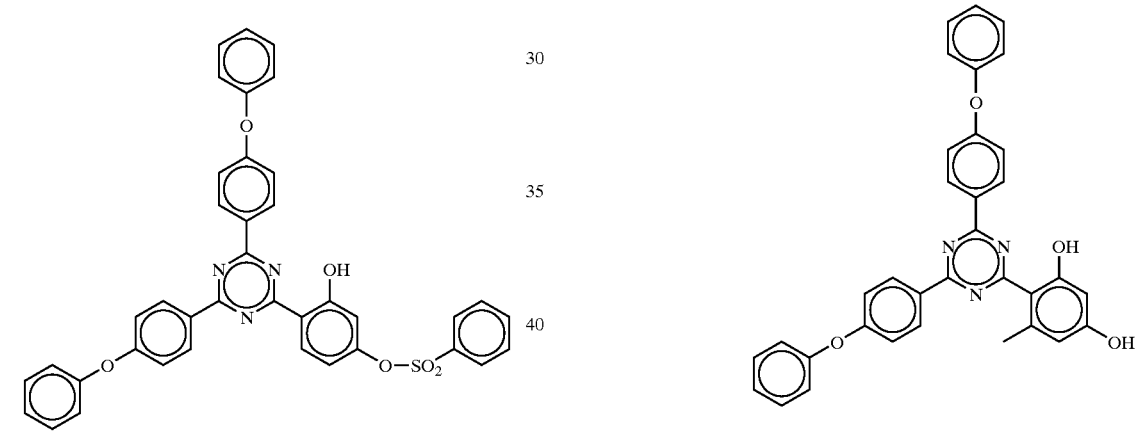

A mixture of 0.9 gm of 2-chloro-4,6-bis(4-phenoxyphenyl)-1,3,5-triazine, 0.24 gm of m-cresol and 0.4 gm $AlCl_3$ in 5 ml chlorobenzene was heated to 70° C. under nitrogen and efficient stirring. After about 4 hr at 70° C., the reaction mixture was analyzed by HPLC, which showed the formation of a new product, and almost disappearance of the starting triazine. The reaction mixture was cooled to room temperature and quenched with water. It was then extracted with methylene chloride, and the organic layer separated, washed with water, dried, and concentrated to give a crude product. The crude product was crystallized from acetone to give almost pure 2-(2-hydroxy-4-methylphenyl)-4,6-bis(4-phenoxyphenyl)-1,3,5-triazine identified by HPLC, NMR and mass spectroscopy.

Example 11

Reaction of 2-chloro-4,6-bis(4-phenoxyphenyl)-1,3,5-triazine with 3,4-diemthylphenol: Preparation of 2-(2-hydroxy-4,5-dimethylphenyl)-4,6-bis(4-phenoxyphenyl)-1,3,5-triazine

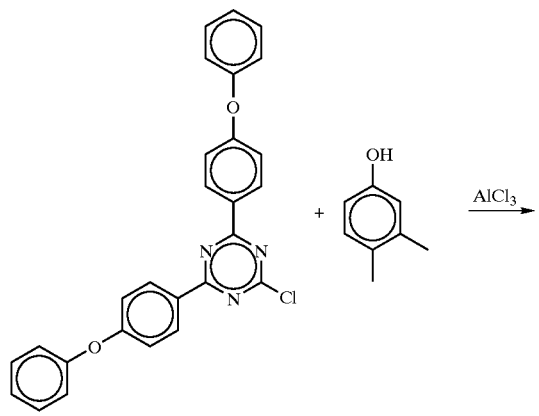

A mixture of 0.9 gm of 2-chloro-4,6-bis(4-phenoxyphenyl)-1,3,5-triazine, 0.27 gm of 3,4-dimethylphenol and 0.4 gm AlCl₃ in 5 ml chlorobenzene was heated to 70° C. under nitrogen and efficient stirring. After 8 hr at 70° C., the reaction mixture was cooled to room temperature and quenched with water. The crude product obtained after distilling off chlorobenzene was shown to contain the product 2-(2-hydroxy-4,5-dimethylphenyl)-4,6-bis(4-phenoxyphenyl)-1,3,5-triazine based on HPLC and Mass spectroscopy.

Example 12

Reaction of 2-chloro-4,6-bis(4-phenoxyphenyl)-1,3,5-triazine 4-hexylresorcinol: Preparation of 2-(2,4-dihydroxy-5-hexylphenyl)-4,6-bis(4-phenoxyphenyl)-1,3,5-triazine

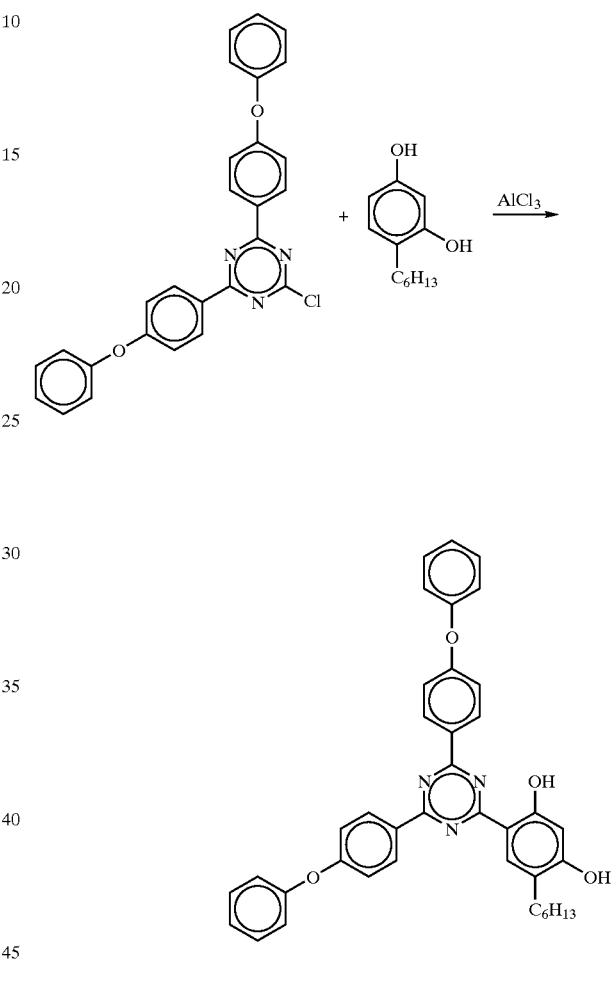

A mixture of 0.9 gm of 2-chloro-4,6-bis(4-phenoxyphenyl)-1,3,5-triazine, 0.39 gm of 4-hexylresorcinol and 0.2 gm AlCl₃ in 5 ml chlorobenzene was heated to 95° C. under nitrogen and efficient stirring. After about 7 hr at 95° C., the reaction mixture was analyzed by HPLC, which showed the formation of a new product, and almost disappearance of the starting triazine. The reaction mixture was cooled to room temperature and quenched with water. It was then extracted with methylene chloride, and the organic layer separated, washed with water, dried, and concentrated to give a crude product. The crude product was analyzed to contain 2-(2,4-dihydroxy-5-hexylphenyl)-4,6-bis(4-phenoxyphenyl)-1,3,5-triazine identified by HPLC, NMR and mass spectroscopy.

Example 13

Reaction of 2-chloro-4,6-bis(4-phenoxyphenyl)-1,3,5-triazine with m-cresol: Preparation of 2-(2-hydroxy-4-methylphenyl)-4,6-bis(4-phenoxyphenyl)-1,3,5-triazine

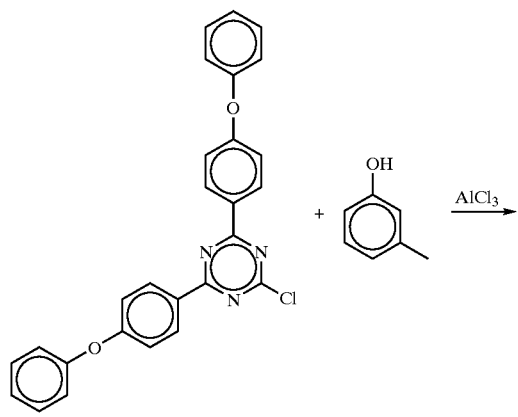

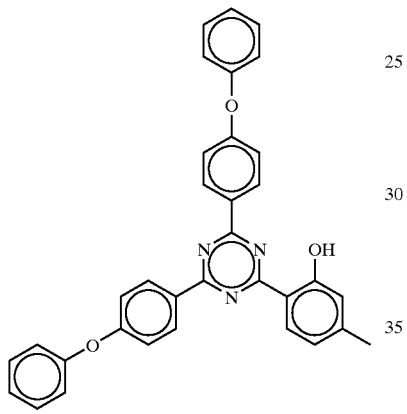

A mixture of 0.9 gm of 2-chloro-4,6-bis(4-phenoxyphenyl)-1,3,5-triazine, 0.24 gm of m-cresol and 0.4 gm $AlCl_3$ in 5 ml chlorobenzene was heated to 70° C. under nitrogen and efficient stirring. After about 4 hr at 70° C., the reaction mixture was analyzed by HPLC, which showed the formation of a new product, and almost disappearance of the starting triazine. The reaction mixture was cooled to room temperature and quenched with water. It was then extracted with methylene chloride, and the organic layer separated, washed with water, dried, and concentrated to give a crude product. The crude product was crystallized from acetone to give pure 2-(2-hydroxy-4-methylphenyl)-4,6-bis(4-phenoxyphenyl)-1,3,5-triazine identified by HPLC, NMR and mass spectroscopy.

Example 14

Reaction of 2-(2,4-dihydroxyphenyl)-4,6-bis(4-phenoxyphenyl)-1,3,5-triazine with 1,8-diiodooctane: Preparation of a Triazine Dimer

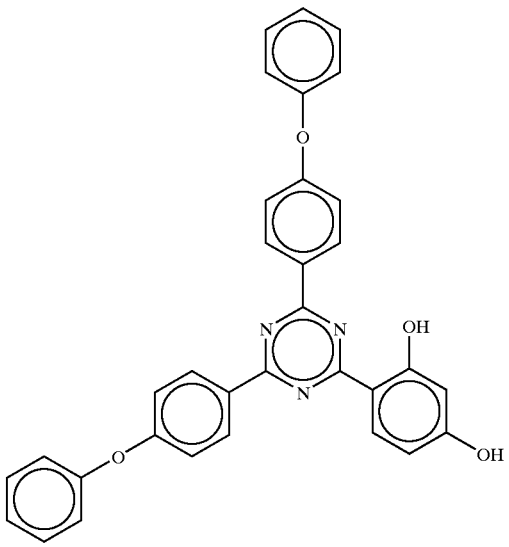

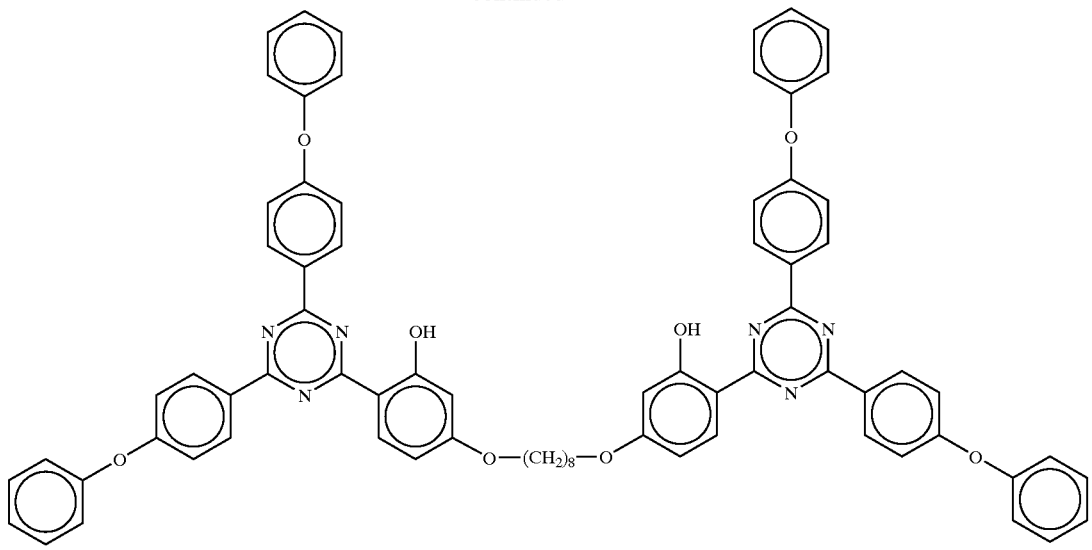

To a stirring mixture of 5 gm of 2-(2,4-dihydroxyphenyl)-4,6-bis(4-phenoxyphenyl)-1,3,5-triazine, 10 gm of potassium carbonate and 0.5 gm of Aliquat 336 in 25 ml of MIBK was added 1,8-diiodooctane. The reaction mixture was heated to reflux for 10 hr. The reaction mixture was then cooled to room temperature, diluted with methylene chloride, and filtered through Celite. The filtrate was concentrated to give the crude product containing the desired dimer product identified based on HPLC and mass spectroscopy.

Example 15

Preparation of 2,4-bis(2,4-dihydroxyphenyl)-6-(4-phenoxyphenyl)-1,3,5-triazine

To a stirring mixture of 9 gm of cyanuric chloride, 20 gm of aluminum chloride in 50 mL of o-dichlorobenzene was added 8.5 gm of phenyl ether followed by 11 gm of resorcinol. The reaction mixture was first stirred at room temperature and then gradually heated to 110–115° C., and then held for 4 hr at this temperature. The heating was discontinued, and the reaction mixture quenched with water. O-Dichlorobenzene was removed azeotropically from the product mixture, the precipitated material filtered, and washed with water. The crude product was purified by column chromatography to give 2.3 gm of pure 2,4-bis(2,4-dihyroxyphenyl)-6-(4-phenoxyphenyl)-1,3,5-triazine, identified by HPLC, NMR, LC-UV and mass spectroscopy.

Example 16

Reaction of 2,4-bis(2,4-dihydroxyphenyl)-6-(4-phenoxyphenyl)-1,3,5-triazine with n-octyl Iodide: Preparation of 2-(2-hydroxy-4-octyloxyphenyl)-4-(2,4-dihydroxyphenyl)-6-(4-phenoxyphenyl)-1,3,5-triazine and 2,4-bis(2-hydroxy-4-octyloxyphenyl)-6-(4-phenoxyphenyl)-1,3,5-triazine

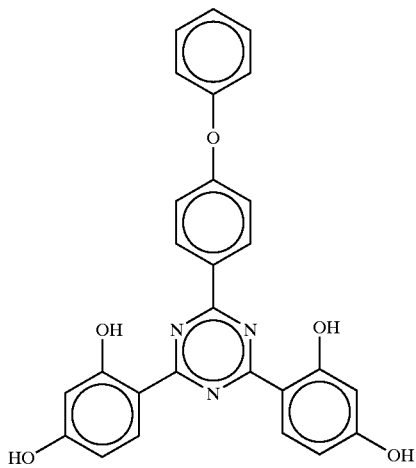

$C_8H_{17}I$; MIBK
$K_2CO_3$

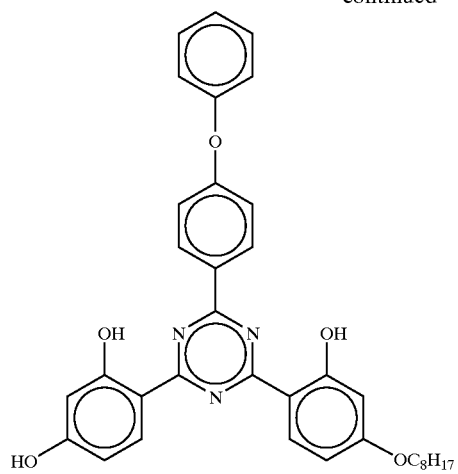

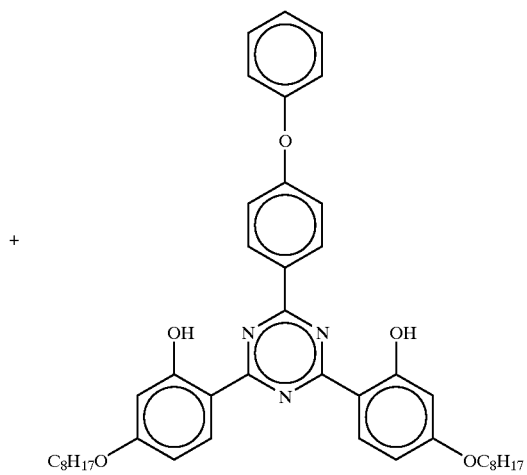

A mixture of 1 gm 2,4-bis(2,4-dihydroxyphenyl)-6-(4-phenoxyphenyl)-1,3,5-triazine, 0.36 gm 1-iodooctane, 1.4 gm anhydrous potassium carbonate, 0.2 gm Aliquat 336 and 10 mL MIBK was heated to reflux for 8 hr. The reaction mixture was cooled to room temperature, diluted with methylene chloride, and filtered through Celite. The filtrate was concentrated under reduced pressure. The residue thus obtained was analyzed by HPLC, LCUV and LCMS to contain a mixture of 2-(2-hydroxy-4-octyloxyphenyl)-4-(2,4-dihydroxyphenyl)-6-(4-phenoxyphenyl)-1,3,5-triazine and 2,4-bis(2-hydroxy-4-octyloxyphenyl)-6-(4-phenoxyphenyl)-1,3,5-triazine and some unreacted 2,4-bis(2,4-dihydroxyphenyl)-6-(4-phenoxyphenyl)-1,3,5-triazine. Performance of the Triazine Light Stabilizer of the Invention Compared to Conventional Triazine Light Stabilizers Examples 17 to 19

Preparation of Performance Samples Containing 2-(2-hydroxy-4-octyloxyphenyl)-4,6-bis(4-phenoxyphenyl)-1,3,5-triazine (Compound A) and other Commercial UV Absorbers in Polycarbonate Plaques Compound A, 2-(2-hydroxy-4-octyloxyphenyl)-4,6-bis(4-phenoxyphenyl)-1,3,5-triazine, at a loading level of 0.35% by weight and 0.05% phosphite (Ultranox 641, commercially available from General Electric Specialty Chemicals of Morgantown, W. Va.) was dry blended into a Lexan 101-1111 polycarbonate pellets (containing 0.5% phosphite) or Lexan 100 virgin polycarbonate flakes (both commercially available from General Electric Specialty Chemicals of Morgantown, W. Va.). The blended material was melt mixed and then extruded in a Brabender PL-2000 torque rheometer (commercially available from Pasedena Hydraulics of The City of Industry, CA) equipped with a single mixing screw extruder at 300° C. The extrudate was cooled dried and pellitized. The pellets were injection molded into sample plaques (2 inches×2.5 inches×125 mils) using an Arburg Allrounder 320-210-750 injection molding machine (commercially available from Arbury GmbH & Co. of Lossburg, Germany) at 300° C. Plaques with a commercially available triazine light stabilizer, TINUVIN® 1577, a product of Ciba Specialty Chemicals, [2-(2-hydroxy-4-hexyloxyphenyl)-4,6-bis(phenyl)-1,3,5-triazine] and control plaques without any UV absorber were prepared in an identical manner.

Examples 20 to 22

Effects of Weathering on UV Stabilized Plaques

Sample plaques were subjected to xenon-arc accelerated weathering. Xenon-arc accelerated weathering was carried out by exposing the sample plaques in a xenon-arc weatherometer as determined by the ASTM G-155 Standard using Test Method B. Discoloration as measured by yellowing index (YI) as a function of weathering time. Color development was determined with a Macbeth Color Eye Colorimeter under laboratory conditions with illuminate C, 2° observer, specular component excluded, and UV component included.

Table 1 below shows the effect of xenon-arc accelerated weathering, as measured by YI (yellow index) values, for polycarbonate plaques containing 0.35% by weight of Compound A, TINUVIN1577 (Tin-1577), and blank polycarbonate plaques for control. An increase in YI indicates an unfavorable discoloration of the polycarbonate.

TABLE 1

| | Xenon-Arc Accelerated Weathering Of A Polycarbonate UV Stabilized Plaque | | | |
|---|---|---|---|---|
| Example | Additive | YI T = 0 hr | YI T = 400 hr | YI T = 800 hr | YI T = 1200 hr |
| 20 | Compound A | 6.2 | 12.9 | 15.4 | 16.8 |
| 21 | Tin-1577 | 8.3 | 14 | 16.1 | 17.3 |
| 22 | PC blank | 3.1 | 20.9 | 24.3 | 29.9 |

The results in Table 1 show that the initial YI for compound A compared to the commercially available product is significantly better resulting in less initial discoloration of the polycarbonate plaques. The results also demonstrate that the polycarbonate plaque stabilized with Compound A showed equal or improved performance compared to the polycarbonate plaques containing TINUVIN 1577 and no stabilizer when the plaques were subjected to xenon-arc accelerated weathering.

Examples 23 to 24

Effect on Severe Molding Conditions on UV Stabilizer Polycarbonate Plaques

Table 2 shows the effect on YI values of exposing the polycarbonate pellets to severe conditions during the injection molding process used to manufacture the plaques. The plaques contained 0.35% by weight of the UV stabilizers compounds and 0.05% of a phosphite. As noted above, plaques are typically processed with temperatures up to 300° C. Under the severe conditions the plaques are processed at a temperature of 340° C. with the compound filling the length of the injection molder barrel for either 40 seconds (refer to as severe 40 seconds) or for 5 minutes (refer to as severe 5 minutes).

TABLE 2

Effect of Severe Injection Molding Conditions on YI Values

| Example | Additive | YI Normal (40 sec at 300° C.) | YI Severe (40 sec at 340° C.) | YI Severe (5 min at 340° C.) |
|---|---|---|---|---|
| 23 | Compound A | 6.2 | 6.9 | 8.2 |
| 24 | Tin-1577 | 8.3 | 7.6 | 8.5 |

The results in Table 2 demonstrate that the stability of polycarbonate plaques containing Compound A was marginally superior to the stability of polycarbonate plaques containing 0.35% of TINUVIN 1577 as measured by YI values, when the plaques were subjected to severe processing conditions.

Overall the results show that Compound A is effective at stabilizing polymeric compounds, such as polycarbonates, against discoloration. Moreover, the results demonstrate that Compound A is superior to a similar commercially available conventional triazine light stabilizer in initial discoloration, and equal or marginally better when subject to accelerated weathering and severe molding conditions.

The invention described and claimed herein is not to be limited in scope by the specific embodiments herein disclosed, since these embodiments are intended as illustrations of several aspects of the invention Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:
1. A compound of Formula I

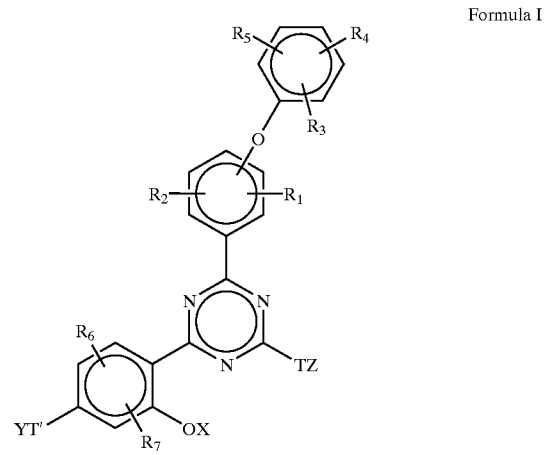

Formula I wherein $R_1$, $R_2$, $R_3$, $R_4$, $R_5$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_1$ and $R_2$, $R_3$ and $R_4$, or $R_4$ and $R_5$, taken together being a part of a saturated or unsaturated fused carbocyclic ring optionally containing O, N, or S atoms in the ring;

each of T and T' is independently a direct bond, oxygen, NR, sulfur or a functional group containing these elements;

X is independently selected from hydrogen and a blocking group selected from one or more of the following groups: allyl, —$COR^a$, —$SO_2R^b$, —$SiR^cR^dR^e$, —$PR^fR^g$, —$POR^fR^g$ and —$CONHR^h$, wherein
each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;

each $R^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each $R^h$ is independently selected from $C_1$–$C_8$ alkyl, $C_5$–$C_{12}$ cycloalkyl, $C_2$–$C_8$ alkenyl, —$CH_2$—CO—$CH_3$, and phenyl which is unsubstituted or substituted by $C_1$–$C_{12}$ alkyl, $C_2$–$C_8$ alkenyl, $C_1$–$C_4$ alkoxy, halogen and/or benzyl;

each of Y, $R_6$ and $R_7$ are each independently hydrogen, hydrocarbyl group, a functional hydrocarbyl group, halogen, hydroxyl, cyano, —O(hydrocarbyl), —O(functional hydrocarbyl), —N(hydrocarbyl)$_2$, —N(functional hydrocarbyl)$_2$, —N(hydrocarbyl)(functional hydrocarbyl), —S(hydrocarbyl), —S(functional hydrocarbyl), —SO$_2$(hydrocarbyl), —SO$_2$(functional hydrocarbyl), —SO$_3$(hydrocarbyl), —SO$_3$(functional hydrocarbyl), —CO$_2$(hydrocarbyl), —CO$_2$(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)$_2$, —CON(hydrocarbyl)(functional hydrocarbyl), —CON(functional hydrocarbyl)$_2$, wherein the hydrocarbyl or functional hydrocarbyl may be the same or different and has 1 to 24 carbon atoms;

Z is Y,

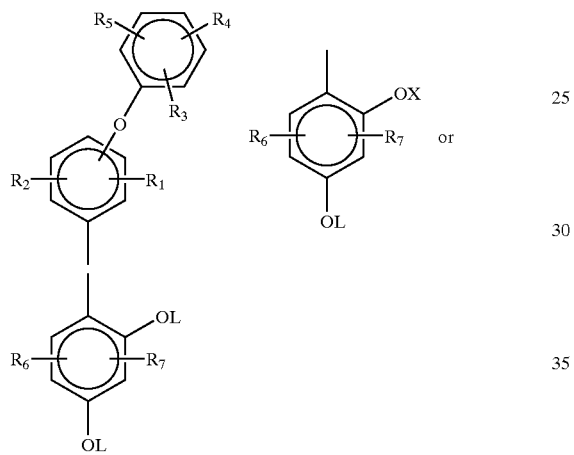

and wherein L is selected from the group consisting of: hydrogen; an alkyl of 1 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an alkenyl of 2 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an aralkyl of 7 to 24 carbon atoms optionally substituted by one or more hydroxy, alkoxy, chloro, cyano, carboxy, carboalkoxy, amino, amido, carbamato, or epoxy groups, and which may contain one or more carbonyl groups, oxygen atoms or nitrogen atoms in the chain.

2. A compound according to claim 1 wherein T' is an oxygen atom.

3. A compound according to claim 1 wherein TZ is

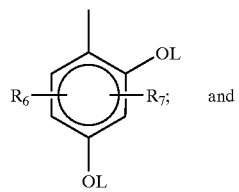

$R_6$ and $R_7$ are independently hydrogen, hydrocarbyl, functional hydrocarbyl, halogen, hydroxyl, —O(hydrocarbyl), —O(functional hydrocarbyl), —S(hydrocarbyl), —SO$_2$(hydrocarbyl), —SO$_3$(hydrocarbyl), —COO(hydrocarbyl), —CO(hydrocarbyl), —OCO(hydrocarbyl), —N(hydrocarbyl)(hydrocarbyl), —S(functional hydrocarbyl), —SO$_2$(functional hydrocarbyl), —SO$_3$(functional hydrocarbyl), —COO(functional hydrocarbyl), —CO(functional hydrocarbyl), —OCO(functional hydrocarbyl), —N(functional hydrocarbyl)(functional hydrocarbyl) or cyano.

4. A compound according to claim 2 wherein $R_1$ to $R_7$ and X are hydrogen, and TZ is

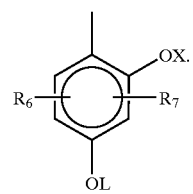

5. A compound according to claim 1 wherein TZ is:

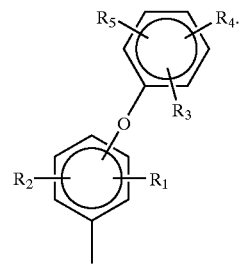

6. A compound according to claim 5 wherein T is oxygen.

7. A compound according to claim 6 wherein $R_1$ to $R_7$ and X are hydrogen.

8. A compound of Formula VI:

(Formula VI)

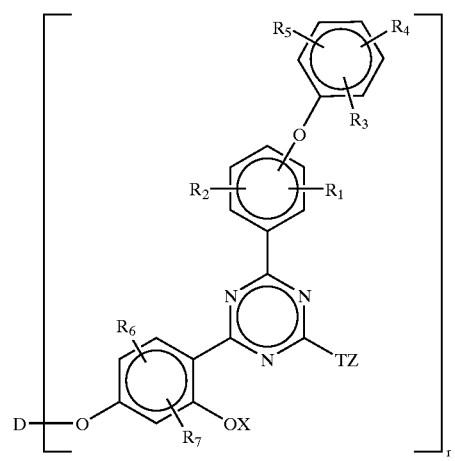

wherein $R_1$, $R_2$, $R_3$, $R_4$, $R_5$ are the same or different and each is hydrogen, halogen, alkyl, of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbon atoms, and optionally with either of $R_1$, and $R_2$, $R_3$ and $R_4$, or $R_4$ and $R_5$, taken together being a part of a saturated or unsaturated fused carbocyclic ring optionally containing O, N, or S atoms in the ring;

T is a direct bond, oxygen, NR, sulfur or a functional group containing these elements;

X is independently selected from hydrogen and a blocking group selected from one or more of the following groups: allyl, $—COR^a$, $—SO_2R^b$, $—SiR^cR^dR^e$, $—PR^fR^g$, $—POR^fR^g$ and $—CONHR^h$, wherein each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, $—CH_2—CO—CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;

each $R^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each $R^h$ is independently selected from $C_1$–$C_8$ alkyl, $C_5$–$C_{12}$ cycloalkyl, $C_2$–$C_8$ alkenyl, $—CH_2—CO—CH_3$, and phenyl which is unsubstituted or substituted by $C_1$–$C_{12}$ alkyl, $C_2$–$C_8$ alkenyl, $C_1$–$C_4$ alkoxy, halogen and/or benzyl;

each of Y, $R_6$ and $R_7$ are each independently hydrogen, hydrocarbyl group, a functional hydrocarbyl group, halogen, hydroxyl, cyano, —O(hydrocarbyl), —O(functional hydrocarbyl), —N(hydrocarbyl)$_2$, —N(functional hydrocarbyl)$_2$, —N(hydrocarbyl)(functional hydrocarbyl), —S(hydrocarbyl), —S(functional hydrocarbyl), —SO$_2$(hydrocarbyl), —SO$_2$(functional hydrocarbyl), —SO$_3$(hydrocarbyl), —SO$_2$(functional hydrocarbyl), —CO$_2$(hydrocarbyl), —CO$_2$(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)$_2$, —CON(hydrocarbyl)(functional hydrocarbyl), —CON(functional hydrocarbyl)$_2$, wherein the hydrocarbyl or functional hydrocarbyl may be the same or different and has 1 to 24 carbon atoms;

Z is Y,

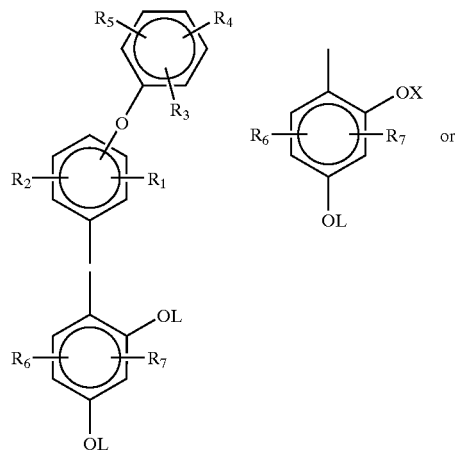

and wherein L is selected from the group consisting of: hydrogen; an alkyl of 1 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an alkenyl of 2 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an aralkyl of 7 to 24 carbon atoms optionally substituted by one or more hydroxy, alkoxy, chloro, cyano, carboxy, carboalkoxy, amino, amido, carbamato, or epoxy groups, and which may contain one or more carbonyl groups, oxygen atoms or nitrogen atoms in the chain;

and r is an integer between 2 and 4;

when r is 2, D is selected from the group consisting of $C_2$–$C_{16}$ alkyl, $C_4$–$C_{12}$ alkenyl, xylylene, $C_3$–$C_{20}$ alkyl which is interrupted by one or more oxygen atoms, hydroxy-substituted $C_3$–$C_{20}$ alkyl which is interrupted by one or more oxygen atoms, $—CH_2CH(OH)CH_2O—R^{15}—OCH_2CH(OH)CH_2—$, $—CO—R^{16}—CO—$, $—CO—NH—R^{17}—NH—CO—$, $—(CH_2)_s—COO—R^{18}—OCO—(CH_2)_s—$ a polyoxyalkylene bridge member of the Formula XX $$—CH_2—CH(OH)—CH_2—O—(CH_2—(CH_2)_u—O—)_{mm}—CH_2CH(OH)—CH_2— \qquad (XX),$$

a polyoxyalkylene bridge member of the Formula XXI $$—CO—(CH_2)_u—O—(CH_2—(CH_2)_u—O—)_{mm}—(CH_2)_u—CO \qquad (XXI),$$

a polyoxyalkylene bridge member of the Formula XXII $$—YY—O—CO(CH_2)_u—O—(CH_2—(CH_2)_u—O—_{mm}—(CH_2)_u—COO—YY— \qquad (XXII),$$

a polyoxyalkylene bridge member of the Formula XXIII $$—(CH_2)_{kk}—CH(R^{21})—CO—B_1—(C_{nn}H_{2nn}—O—)_{mm}C_{nn}H_{2nn}—B_1—CO—CH(R^{21})—(CH_2)_{kk}— \qquad (XXIII),$$

a polyoxyalkylene bridge member of the Formula XXIV

—COC(R²¹)HCH₂NH(C$_{nn}$H$_{2nn}$O)$_m$C$_{nn}$H$_{2nn}$—NHCH₂—
C(R²¹)HCO— (XXIV), a polyoxyalkylene bridge member of the Formula XXV —YY—O—CO—(CH₂)₂—NH—(C$_{nn}$H$_{2nn}$—O—)$_{mm}$—C$_{nn}$H$_{2nn}$—
NH—(CH₂)₂COO—YY— (XXV), a polyoxyalkylene bridge member of the Formula XXVI —(C$_{nn}$H$_{2nn}$—O—)$_{mm}$C$_{nn}$H$_{2nn}$— (XXVI), and a polyoxyalkylene bridge member of the Formula XXVII —CH(CH₃)—CH₂—(O—CH(CH₃)—CH₂)$_a$—(O—CH₂CH₂)$_b$—
(O—CH₂—CH(CH₃)$_c$— (XXVII), wherein a+c=2.5 and b=8.5 to 40.5 or a+c=2 to 33 and b=0,
$R^{21}$ is hydrogen or $C_1$–$C_{16}$ alkyl,
YY is unsubstituted or substituted $C_2$–$C_{20}$ alkyl,
kk is zero or an integer from 1–16,
$B_1$ is O or NH,
mm is an integer from 2 to 60,
nn is an integer from 2 to 6,
u is an integer from 1 to 4;
when r is 3, D is —[—(CH₂)$_s$—COO—]₃—R¹⁹
and when r is 4, D is —[—(CH₂)$_s$—COO—]₄—R²⁰
wherein $R^{19}$ is $C_3$–$C_{10}$ alkanetriyl and $R^{20}$ is $C_4$–$C_{10}$ alkanetetryl; and
s is 1–6;
$R^{15}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl, or phenylene-XX-phenylene wherein XX is —O—, —S—, —SO₂—, —CH₂—, or —C(CH₃)₂;
$R^{16}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl provided that when r is 3 the alkenyl has at least 3 carbons;
$R^{17}$ is $C_2$–$C_{10}$ alkyl, phenyl, naphthyl, diphenyl, or $C_2$–$C_6$ alkenyl, methylenediphenylene, or $C_4$–$C_{15}$ alkylphenyl; and
$R^{18}$ is $C_2$–$C_{10}$ alkyl, or $C_4$–$C_{20}$ alkyl interrupted by one or more oxygen atoms.

9. A compound of Formula (VII):

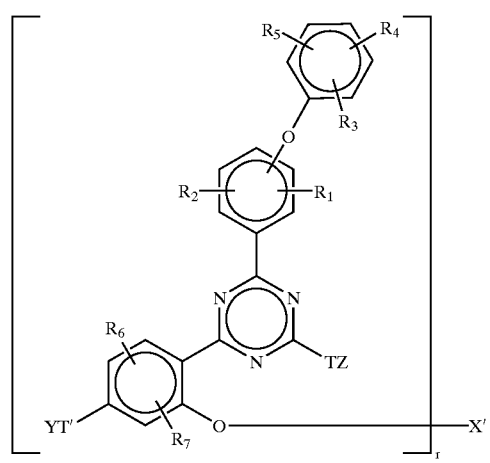

(Formula VII)

wherein $R_1$, $R_2$, $R_3$, $R_4$, $R_5$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, SO₂R, SO₃H, SO₃M, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_1$ and $R_2$, $R_3$ and $R_4$, or $R_4$ and $R_5$, taken together being a part of a saturated or unsaturated fused carbocyclic ring optionally containing O, N, or S atoms in the ring;

each of T and T' is independently a direct bond, oxygen, NR, sulfur or a functional group containing these elements;

X is independently selected from hydrogen and a blocking group selected from one or more of the following groups: allyl, —COR$^a$, —SO₂R$^b$, —SiR$^c$R$^d$R$^e$, —PR$^f$R$^g$, —POR$^f$R$^g$ and —CONHR$^h$, wherein each R$^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —CH₂—CO—CH₃, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;

each R$^b$ is independently selected from $C_1$–$C_{12}$ alkyl, $C_6$–$C_{10}$ aryl and $C_7$–$C_{18}$ alkylaryl;

each R$^c$, R$^d$ and R$^e$ is independently selected from $C_1$–$C_{18}$ alkyl, cyclohexyl, phenyl and $C_1$–$C_{18}$ alkoxy;

each R$^f$ and R$^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each R$^h$ is independently selected from $C_1$–$C_8$ alkyl, $C_5$–$C_{12}$ cycloalkyl, $C_2$–$C_8$ alkenyl, —CH₂—CO—CH₃, and phenyl which is unsubstituted or substituted by $C_1$–$C_{12}$ alkyl, $C_2$–$C_8$ alkenyl, $C_1$–$C_4$ alkoxy, halogen and/or benzyl;

each of Y, $R_6$ and $R_7$ are each independently hydrogen, hydrocarbyl group, a functional hydrocarbyl group, halogen, hydroxyl, cyano, —O(hydrocarbyl), —O(functional hydrocarbyl), —N(hydrocarbyl)₂, —N(functional hydrocarbyl)₂, —N(hydrocarbyl)(functional hydrocarbyl), —S(hydrocarbyl), —S(functional hydrocarbyl), —SO₂(hydrocarbyl), —SO₂(functional hydrocarbyl), —SO₃(hydrocarbyl), —SO₃(functional hydrocarbyl), —CO₂(hydrocarbyl), —CO₂(functional hydrocarbyl), —CO(hydrocarbyl), —CO(functional hydrocarbyl), —OCO(hydrocarbyl), —OCO(functional hydrocarbyl), —CONH₂, —CONH(hydrocarbyl), —CONH(functional hydrocarbyl), —CON(hydrocarbyl)₂, —CON(hydrocarbyl)(functional hydrocarbyl), —CON(functional hydrocarbyl)₂, wherein the hydrocarbyl or functional hydrocarbyl may be the same or different and has 1 to 24 carbon atoms;

Z is Y,

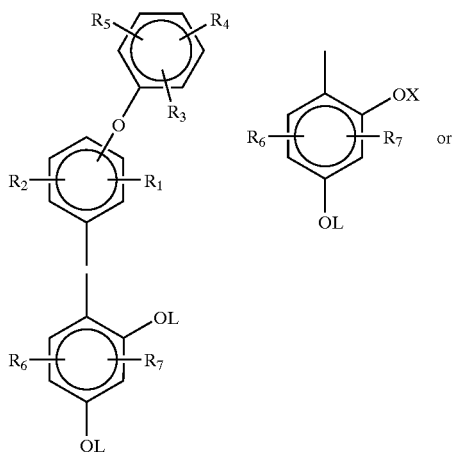

and wherein L is selected from the group consisting of:
hydrogen; an alkyl of 1 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an alkenyl of 2 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an aralkyl of 7 to 24 carbon atoms optionally substituted by one or more hydroxy, alkoxy, chloro, cyano, carboxy, carboalkoxy, amino, amido, carbamato, or epoxy groups, and which may contain one or more carbonyl groups, oxygen atoms or nitrogen atoms in the chain;

r is 2 or 3;

when r is 2, X' is —CO—$R^{16}$—CO—, —$CO_2$—$R^{16}$—$CO_2$—, —$SO_2$—$R^{16}$—$SO_2$—, —CO—NH—$R^{17}$—NH—CO—, a polyoxyalkylene bridge member of Formula

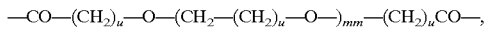

or

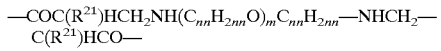

when r=3, X' is

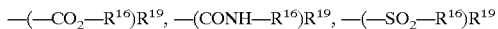

wherein $R^{19}$ is $C_3$–$C_{10}$ alkanetriyl and $R^{16}$ is $C_2$–$C_{10}$ alkyl, $C_2$–$C_{10}$ oxaalkyl or $C_2$–$C_{10}$ dithiaalkyl, phenyl, naphthyl, diphenyl, or $C_2$–$C_6$ alkenyl provided that when r is 3 the alkenyl has at least 3 carbons;

$R^{17}$ is $C_2$–$C_{10}$ alkyl, phenyl, naphthyl, diphenyl, or $C_2$–$C_8$ alkenyl, methylenediphenylene, or $C_4$–$C_{15}$ alkylphenyl;

$R^{21}$ is hydrogen or $C_1$–$C_{16}$ alkyl; and mm is an integer from 2 to 60,
nn is an integer from 2 to 6,
u is an integer from 1 to 4.

10. A compound of Formula (VIII):

(Formula VIII)

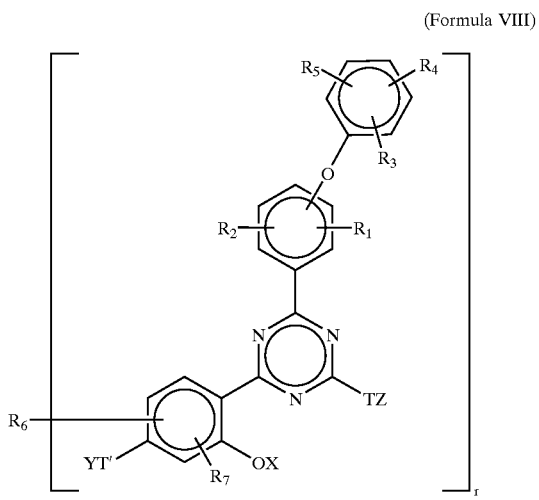

wherein $R_1$, $R_2$, $R_3$, $R_4$, $R_5$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbon atoms, and optionally with either $R_1$ and $R_2$, $R_3$ and $R_4$, or $R_4$ and $R_5$, taken together being a part of a saturated or unsaturated fused carbocyclic ring optionally containing O, N, or S atoms in the ring;

each of T and T' is independently a direct bond, oxygen, NR, sulfur or a functional group containing these elements;

X is independently selected from hydrogen and a blocking group selected from one or more of the following groups: allyl, —$COR^a$, —$SO_2R^b$, —$SiR^c R^d R^e$, —$PR^f R^g$, —$POR^f R^g$ and —$CONHR^h$, wherein each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;

each $R^b$ is independently selected from $C_1$–$C_{12}$ alkyl, $C_6$–$C_{10}$ aryl and $C_2$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each $R^h$ is independently selected from $C_1$–$C_8$ alkyl, $C_5$–$C_{12}$ cycloalkyl, $C_2$–$C_8$ alkenyl, —$CH_2$—CO—$CH_3$, and phenyl which is unsubstituted or substituted by $C_1$–$C_{12}$ alkyl, $C_2$–$C_8$ alkenyl, $C_1$–$C_4$ alkoxy, halogen and/or benzyl;

each of Y and $R_7$ are each independently hydrogen, hydrocarbyl group, a functional hydrocarbyl group, halogen, hydroxyl, cyano, —O(hydrocarbyl), —O(functional hydrocarbyl), —N(hydrocarbyl)$_2$, —N(functional hydrocarbyl)$_2$, —N(hydrocarbyl)(functional hydrocarbyl), —S(hydrocarbyl), —S(functional hydrocarbyl), —SO$_2$(hydrocarbyl), —SO$_2$(functional hydrocarbyl), —SO$_3$(hydrocarbyl), —SO$_3$(functional hydrocarbyl), —CO$_2$(hydrocarbyl), —CO$_2$(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)$_2$, —CON(hydrocarbyl)(functional hydrocarbyl), —CON(functional hydrocarbyl)$_2$, wherein the hydrocarbyl or functional hydrocarbyl may be the same or different and has 1 to 24 carbon atoms;

Z is Y,

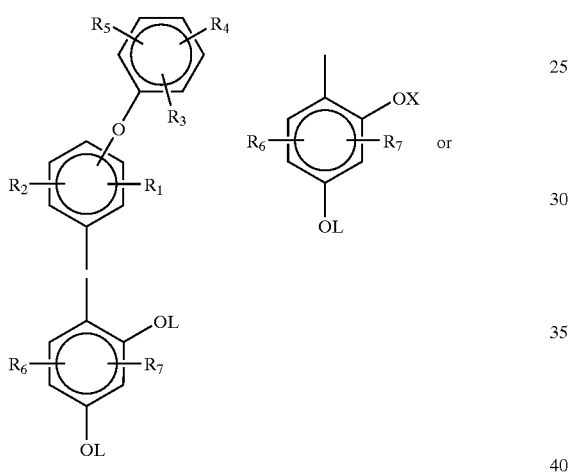

and wherein L is selected from the group consisting of: hydrogen; an alkyl of 1 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an alkenyl of 2 to 24 carbon atoms optionally substituted by one or more hydroxy, alkoxy, carboxy, carboalkoxy, amino, amido, carbamato, or epoxy groups, and which may contain one or more carbonyl groups, oxygen atoms or nitrogen atoms in the chain; an aralkyl of 7 to 24 carbon atoms optionally substituted by one or more hydroxy, alkoxy, chloro, cyano, carboxy, carboalkoxy, amino, amido, carbamato, or epoxy groups, and which may contain one or more carbonyl groups, oxygen atoms or nitrogen atoms in the chain;

$R_6$ is selected from the group consisting of straight chain alkyl of 1 to 12 carbon atoms, branched chain alkyl of 1 to 12 carbon atoms, cycloalkyl 5 to 12 carbon atoms, alkyl substituted by cyclohexyl, alkyl interrupted by cyclohexyl, alkyl substituted by phenylene, alkyl interrupted by phenylene, benzylidene, —S—, —S—S—, —S—E—S—, —SO—, —SO$_2$—, —SO—E—SO—, —SO$_2$—E—SO$_2$—, —CH$_2$—NH—E—NH—CH$_2$—, and

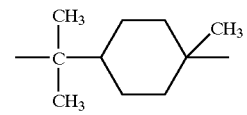

wherein E is selected from the group consisting of alkyl of 2 to 12 carbon atoms, cycloalkyl of 5 to 12 carbon atoms, alkyl interrupted by cyclohexyl of 8 to 12 carbon atoms, alkyl terminated by cyclohexyl of 8 to 12 carbon atoms; and r is an integer between 2 and 4.

11. A compound of Formula IX

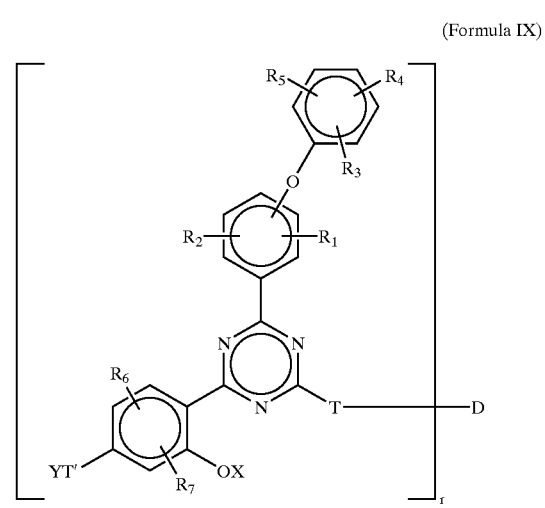

(Formula IX)

wherein $R_1$, $R_2$, $R_3$, $R_4$, $R_5$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbon atoms, and optionally with either of $R_1$ and $R_2$, $R_3$ and $R_4$, or $R_4$ and $R_5$, taken together being a part of a saturated or unsaturated fused carbocyclic ring optionally containing O, N, or S atoms in the ring;

each of T and T' is independently a direct bond, oxygen, NR, sulfur or a functional group containing these elements;

X is independently selected from hydrogen and a blocking group selected from one or more of the following groups: allyl, —COR$^a$, —SO$_2$R$^b$, —SiR$^c$R$^d$R$^e$, —PR$^f$R$^g$, —POR$^f$R$^g$ and —CONHR$^h$, wherein
each R$^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —CH$_2$—CO—CH$_3$, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;

each R$^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each $R^h$ is independently selected from $C_1$–$C_8$ alkyl, $C_5$–$C_{12}$ cycloalkyl, $C_2$–$C_8$ alkenyl, —$CH_2$—$CO$—$CH_3$, and phenyl which is unsubstituted or substituted by $C_1$–$C_{12}$ alkyl, $C_2$–$C_8$ alkenyl, $C_1$–$C_4$ alkoxy, halogen and/or benzyl;

each of Y, $R_6$ and $R_7$ are each independently hydrogen, hydrocarbyl group, a functional hydrocarbyl group, halogen, hydroxyl, cyano, —O(hydrocarbyl), —O(functional hydrocarbyl), —N(hydrocarbyl)$_2$, —N(functional hydrocarbyl)$_2$, —N(hydrocarbyl) (functional hydrocarbyl), —S(hydrocarbyl), —S(functional hydrocarbyl), —SO$_2$(hydrocarbyl), —SO$_2$(functional hydrocarbyl), —SO$_3$(hydrocarbyl), —SO$_3$(functional hydrocarbyl), —CO$_2$(hydrocarbyl), —CO$_2$(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)$_2$, —CON(hydrocarbyl) (functional hydrocarbyl), —CON(functional hydrocarbyl)$_2$, wherein the hydrocarbyl or functional hydrocarbyl may be the same or different and has 1 to 24 carbon atoms;

r is an integer between 2 and 4;

when r is 2, D is selected from the group consisting of $C_2$–$C_{16}$alkylene, $C_4$–$C_{12}$alkenylene, xylylene, $C_3$–$C_{20}$alkylene which is interrupted by one or more oxygen atoms, hydroxy-substituted $C_3$–$C_{20}$alkylene which is interrupted by one or more oxygen atoms, —$CH_2CH(OH)CH_2O$—$R^{15}$—$OCH_2CH(OH)CH_2$, —$CO$—$R^{16}$—$CO$—, —$CO$—$NH$—$R^{17}$—$NH$—$CO$—, and —$(CH_2)_s$—$COO$—$R^{18}$—$OCO$—$(CH_2)_s$—; and when r is 3, D is —[—$(CH_2)_s$—$COO$—]$_3$—$R^{19}$ and when r 4, D is —[—$(CH_2)_s$—$COO$—]$_4$—$R^{20}$ wherein $R^{19}$ is $C_3$–$C_{10}$alkanetriyl and $R^{20}$ is $C_4$–$C_{10}$alkanetetryl;

s is 1–6;

$R^{15}$ is $C_2$–$C_{10}$ alkylene phenylene or a phenylene-x-phenylene- group, wherein X is —O—, —S—, —SO$_2$—, —CH$_2$—, or —C(CH$_3$)$_2$—;

$R_{16}$ is $C_2$–$C_{10}$ alkylene, $C_2$–$C_{10}$ oxaalkylene or $C_2$–$C_{10}$ dithiaalkylene, phenylene, naphthylene, diphenylene or $C_2$–$C_6$ alkenylene;

$R_{17}$ is $C_2$–$C_{10}$ alkylene, phenylene, naphthylene, methylenediphenylene or $C_7$–$C_{15}$ alkylphenylene, and $R_{18}$ is $C_2$–$C_{10}$ alkylene or $C_4$–$C_{20}$ alkylene which is interrupted by one or more oxygen atoms.

12. A method of stabilizing a material which is subject to degradation by actinic radiation by incorporating said material with the compound of claim 1.

13. The method of claim 12, wherein the amount of the said compound is from about 0.01 to about 20% by weight based on the weight of the material to be stabilized.

14. The method of claim 12, wherein the material to be stabilized is selected from the group consisting of polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, acrylonitrile-butadiene-styrene, styrene acrylonitrileacrylate styrene acrylonitrile, cellulosic acetate butyrate, cellulosic polymers, polyimides, polyamideimides, polyetherimides, polyphenylsulfide, polyphenylene oxide, polysulfones, polyethersulfones, polyvinylchlorides, polycarbonates, polyketones, aliphatic polyketones, thermoplastic olefin, aminoresin cross-linked polyacrylates and polyesters, or polyisocyanate cross-linked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, fibers and combinations thereof.

15. The method of claim 14, wherein the material is a polyolefin, polyamide, polyurethane, polyester or a polycarbonate.

16. The method of claim 12 further comprising incorporation of one or more hindered amine light stabilizers.

17. The method according to claim 16, wherein said hindered amine comprises at least one member of the group consisting of: bis(2,2,6,6-tetramethylpiperidin-4-yl)sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl)n-butyl 3,5-di-tert-butyl-4-hydroxybenzylmalonate; the condensate of 1-(2-hydroxyethyl)-2,2,6,6-tetramethyl-4hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl)nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2, 6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis (2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2, 6,6-tetramethylpiperidine; the condensate of N,N'-bis(2,2,6, 6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines; and the reaction product of 7,7,9,9-tetramethyl-2-cycloundecyl-1-oxa-3,8-diaza-4-oxospiro[4.5]decane and epichlorohydrin.

18. The method according to claim 12 further comprising incorporation of one or more additional UV absorbers wherein the additional UV absorber is a benzotriazole derivative, a triazine derivative, a benzophenone derivative, or a combination thereof.

19. A method of stabilizing a material which is subject to degradation by actinic radiation by incorporating said material with the compound of claims 8, 9, 10 or 11.

20. A composition comprising
    (a) the compound of claim 1; and
    (b) at least one other additive selected from group consisting of: UV stabilizers and antioxidants.

21. The composition of claim 20 wherein said at least one other additive is selected from the group consisting of 2-(2'-hydroxyphenyl)benzotriazoles, oxamides, 2-(2-hydroxphenyl)-1,3,5-triazines, 2-hydroxybenzophenones, sterically hindered amines and hindered phenol antioxidants.

22. The composition of claim 21 wherein said at least other additive is selected from the group consisting of: 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,3,3-tetramethylbutyl)-6-benzotriazol-2-ylphenol], the transesterification product of 2-[3'-tert-butyl-5'-(2-methoxycarbonylethyl)-2'-hydroxyphenyl]benzotriazole with polyethylene glycol 300; bis(2,2,6,6-tetramethylpiperidin-4-yl)sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl)n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl)nitrilotriacetate; tetrakis(2,2,6,6-tetramethylpiperidin-4yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines and the reaction product of 7,7,9,9-tetramethyl-2-cycloundecyl-1-oxa-3,8-diaza-4-oxospiro[4.5]decane and epichlorohydrin; 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1 3,5-triazine; 2-[2-hydroxy-4-(2-hydroxy-3-actyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; 2-(2-hydroxyphenyl)-4-(4-methoxyphenyl)-6-phenyl-1,3,5-triazine, 2,4-dihydroxybenzophenone; 2-hydroxy-4-methoxybenzophenone; 2-hydroxy-4-octyloxybenzophenone; 2-hydroxy-4-decyloxybenzophenone; 2-hydroxy-4-dodecyloxybenzophenone; 2-hydroxy-4-benzyloxybenzophenone, 4,2',4-trishydroxybenzophenone; 2'-hydroxy-4,4'-dimethoxybenzophenone; 1,3,5-tris(2,6-dimethyl-4-tert-butyl-3hydroxybenzyl)isocyanurate; 1,3,5-tris(3,5-di-tert-butyl-4-hydroxybenzyl)isocyanurate; 1,3,5-tris(3,5-di-tert-butyl-4-hydroxybenzyl)-2,4,6-trimethylbenzene; 2,6-di-tert-butyl-4-methylphenol; 2,2'-ethylidene-bis(4,6-di-tert-butylphenol); 1,1,3-tris(5-tert-butyl-4-hydroxy-2-methylphenyl)butane; esters of β-(3,5-di-tert-butyl-4-hydroxyphenyl)propionic acid with mono- or polyhydric alcohols; esters of β-(5-tert-butyl-4-hydroxy-3-methylphenyl)propionic acid with mono- or polyhydric alcohols; dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid; amides of β-(3,5-di-tert-butyl-4-hydroxyphenyl)propionic acid such as N,N'-bis(3,5-di-tert-butyl-4-hydroxyphenylpropionyl) hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

23. The composition of claim 22 wherein TZ is

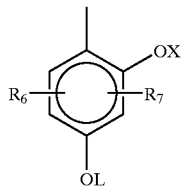

and T' is oxygen, and $R_1$ to $R_7$ and X are hydrogen.

24. The composition of claim 22 wherein TZ is:

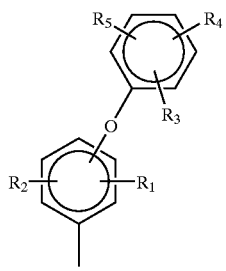

and T' is oxygen, and $R_1$ to $R_7$ and X are hydrogen.

25. The composition of claim 20 comprising a material to be stabilized selected from the group consisting of: polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, acrylonitrile-butadiene-styrene, styrene acrylonitrile, acrylate styrene acrylonitrile, cellulosic acetate butyrate, cellulosic polymers, polyimides, polyamideimides, polyetherimides, polyphenylsulfides, polyphenylene oxide, polysulfones, polyethersulfones, polyvinylchlorides, polycarbonates, polyketonee, aliphatic polyketones, thermoplastic olefin, aminoresin cross-linked polyacrylates and polyesters, polyisocyanate cross-linked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and mixtures thereof.

26. The composition of claim 20 wherein the amount of said compound to said at least one other additive is from about 500:1 to about 1:500 by weight.

27. A composition comprising (a) the compound of claims 9, 10, 11 or 12; and (b) at least one other additive selected from group consisting of: 2-(2'-hydroxy-5'-methylphenyl)-benzotriazole; 2-(3',5'-di-tert-butyl-2-hydroxyphenyl) benzotriazole; 2-(5'-tert-butyl-2'-hydroxyphenyl) benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl) phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl)benzotriazole and 2-(3'-tert-butyl-2'-hydroxy-5'-(2-isooctyloxycarbonylethyl) phenylbenzotriazole; 2,2-methylenebis[4-(1,1,3,3-tetramethylbutyl)-6-benzotriazol-2-ylphenol], the transesterification product of 2-[3'-tert-butyl-5'-(2-methoxycarbonylethyl)-2'-hydroxyphenyl] benzotriazole with polyethylene glycol 300; bis(2,2,6,6-tetramethylpiperidin-4-yl)sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl)n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl) hexamethylenediamine and 4-tert-octylamino-2,6-dichloro-1,3,5-triazine; tris(2,2,6,6-tetramethylpiperidin-4-yl)nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis (1-octyloxy-2,2,6,6-tetramethylpiperidyl)sebacate; bis (1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3, 5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines and the reaction product of 7,7,9,9-tetramethyl-2-cycloundecyl-1-oxa-3,8-diaza-4-oxospiro[4.5]decane and epichlorohydrin; 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; 2-(2-hydroxyphenyl)-4-(4-methoxyphenyl)-6-phenyl-1,3,5-triazine, 2,4-dihydroxybenzophenone; 2-hydroxy-4-methoxybenzophenone; 2-hydroxy-4-octyloxybenzophenone; 2-hydroxy-4-decyloxybenzophenone; 2-hydroxy-4-dodecyloxybenzophenone; 2-hydroxy-4-benzyloxybenzophenone, 4,2',4-trishydroxybenzophenone; 2'-hydroxy4,4'-dimethoxybenzophenone; 1,3,5-tris(2,6-dimethyl-4-tert-butyl-3hydroxybenzyl)isocyanurate; 1,3,5-tris(3,5-di-tert-butyl-4-hydroxybenzyl)isocyanurate; 1,3,5-tris(3,5-di-tert-butyl-4-hydroxybenzyl)-2,4,6-trimethylbenzene; 2,6-di-tert-butyl-4-methylphenol; 2,2'-ethylidene-bis(4,6-di-tert-butylphenol); 1,1,3-tris(5-tert-butyl-4-hydroxy-2-methylphenyl)butane; esters of β-(3,5-di-tert-butyl-4-hydroxyphenyl)propionic acid with mono- or polyhydric alcohols; esters of β-(5-tert-butyl-4-hydroxy-3-methylphenyl)propionic acid with mono- or polyhydric alcohols; dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid; amides of β-(3,5-di-tert-butyl-4-hydroxyphenyl)propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

28. The composition of claim 27 wherein the amount of said compound to said at least one other additive is from about 500:1 to about 1:500 by weight.

29. The composition of claim 27 further comprising a material to be stabilized selected from the group consisting of polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, acrylonitrile-butadiene-styrene, styrene acrylonitrile, acrylate styrene acrylonitrile, cellulosic acetate butyrate, cellulosic polymers, polyimides, polyamideimides, polyetherimides, polyphenylsulfide, polyphenylene oxide, polysulfones, polyethersulfones, polyvinylchlorides, polycarbonates, polyketones, aliphatic polyketones, thermoplastic olefin, aminoresin cross-linked polyacrylates and polyesters, or polyisocyanate cross-linked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, fibers and combinations thereof.

30. A compound having the Formula

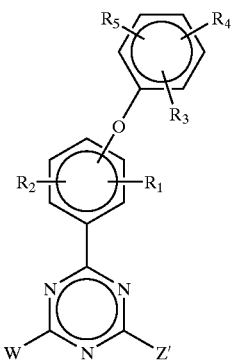

wherein $R_1$, $R_2$, $R_3$, $R_4$, $R_5$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 1 to 24 carbon atoms, cycloacyl of 5 to 24 carbon atoms, aralkyl of 7 to 24 carbon atoms, or aracyl of 6 to 24 carbons atoms, and optionally with either of $R_1$ and $R_2$, $R_3$ and $R_4$, or $R_4$ and $R_5$, taken together being a part of a saturated or unsaturated fused carbocyclic ring optionally containing O, N, or S atoms in the ring:

Z' is a halogen, and W is

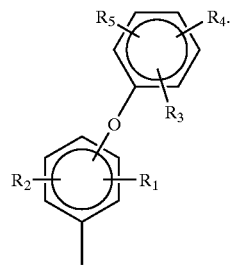

* * * * *

UNITED STATES PATENT AND TRADEMARK OFFICE
CERTIFICATE OF CORRECTION

PATENT NO. : 6,855,269 B2
DATED : February 15, 2005
INVENTOR(S) : Ram Baboo Gupta et al.

It is certified that error appears in the above-identified patent and that said Letters Patent is hereby corrected as shown below:

Column 48,
Line 38, replace "wherein T" -- wherein T' --

Column 49,
Line 57, replace "—$SO_2$(functional hydrocarbyl)" with -- —$SO_3$(functional hydrocarbyl) --

Column 50,
Line 56, replace the entire line to read
-- —CO—$(CH_2)_u$—O—$(CH_2$—$(CH_2)_u$—O—$)_{mm}$—$(CH_2)_u$—CO—
    (XX1), --

Column 51,
Line 14, "$CH_2CH_2$" with -- $CH_2$—$CH_2$ --

Column 53,
Line 53, replace "— $(CONH$—$R^{16})$" with -- —(—CONH— $R^{16}$) --
Line 61, replace "$C_2$-$C_8$" with $C_2$-$C_6$ --

Column 54
Line 56, replace "$C_2$-$C_{18}$" with -- $C_7$-$C_{18}$ --

Column 56,
Line 41, after "atoms," insert -- aracyl of 6 to 24 carbon atoms, OR, NRR', CONRR', OCOR, CN, SR, $SO_2R$, $SO_3H$, $SO_3M$, --

Column 58,
Line 40, replace "4hydroxypiperidine" with -- 4-hydroxypiperidine--

Column 59,
Line 51, replace "(1,3" with -- (1,1,3 --

Column 60,
Line 43, replace "(1 3,5" with -- (1,3,5 --
Line 44, replace "actyloxypropyloxy" with -- octyloxypropyloxy --

Column 61,
Line 41, after "claim 20" insert -- further --
Line 52, replace "polyketonee" with -- polyketones --
Line 9, replace "9, 10, 11 or 12" with -- 8, 9, 10 or 11 --

UNITED STATES PATENT AND TRADEMARK OFFICE
CERTIFICATE OF CORRECTION

PATENT NO. : 6,855,269 B2
DATED : February 15, 2005
INVENTOR(S) : Ram Baboo Gupta et al.

It is certified that error appears in the above-identified patent and that said Letters Patent is hereby corrected as shown below:

Column 62,
Line 12, replace "butyl-2" with -- butyl-2' --

Signed and Sealed this

Seventeenth Day of May, 2005

JON W. DUDAS
*Director of the United States Patent and Trademark Office*